Figure 1:
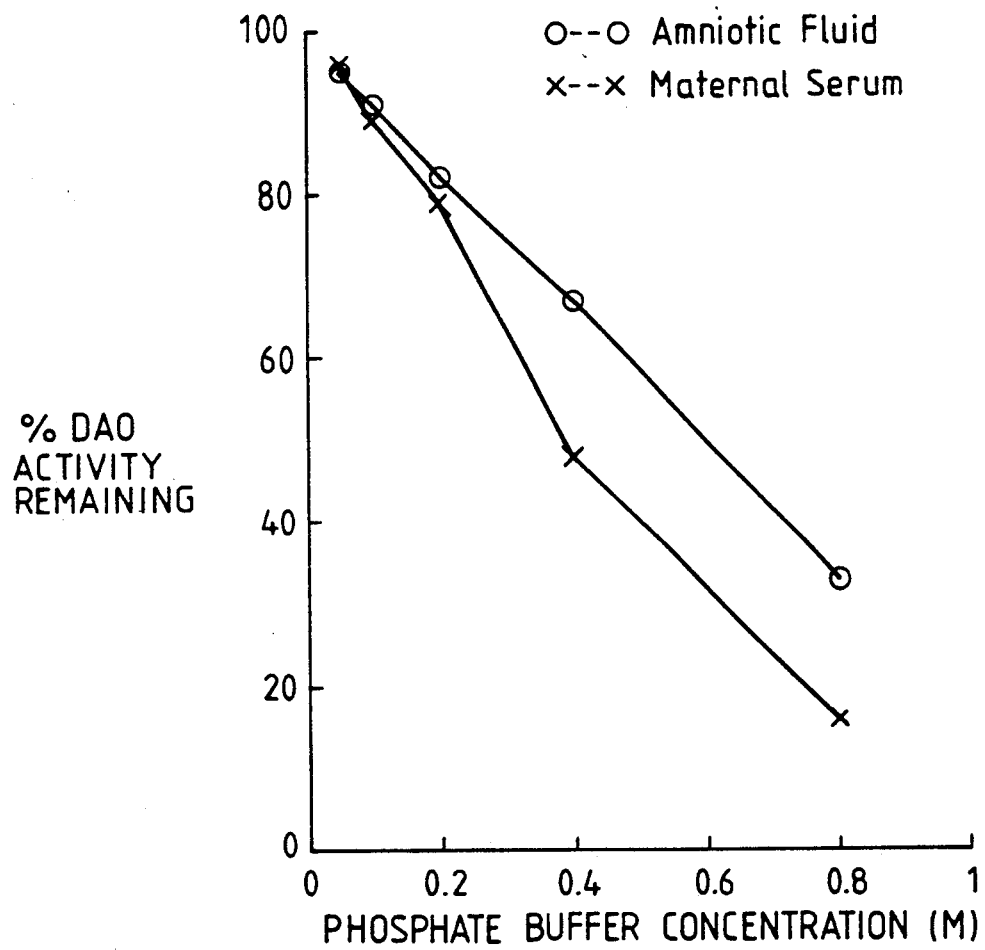

United States Patent [19]

Cowley et al.

[11] Patent Number: 5,284,749
[45] Date of Patent: Feb. 8, 1994

[54] DIAMINE OXIDASE AND ASSAY FOR RUPTURE OF AMNIOTIC MEMBRANE IN PREGNANT MAMMALS

[75] Inventors: David M. Cowley; David J. Maguire; Victor Voroteliak, all of Brisbane, Australia

[73] Assignee: Griffith University, Queensland, Australia

[21] Appl. No.: 623,168

[22] Filed: Oct. 31, 1990

[51] Int. Cl.$^5$ ............... G01N 33/53; G01N 33/536; G01N 33/543; G01N 33/558
[52] U.S. Cl. ....................... 435/7.1; 436/501; 436/514; 436/518; 436/536; 436/548
[58] Field of Search ............ 435/7.1; 436/501, 512, 436/513, 514, 518, 536, 547, 548

[56] References Cited
PUBLICATIONS

Watkins et al. Biosis Abstract No. 64031438 Ann. Clin Lab Sci. 7(3) 1977. 231–240.
Gahl et al. Biosis Ab. No. 75040200 Obstet Gynecol. 60(3) 279–304 (1982).
Oratore et al. FEBS Letters, 104(1) 154–156 (1979).

*Primary Examiner*—Amelia Burgess Yarbrough
*Assistant Examiner*—Lori L. Yuan
*Attorney, Agent, or Firm*—Nixon & Vanderhye

[57] ABSTRACT

Assay for detection of a form of diamine oxidase which is present only in amniotic fluid and, more especially, for detection of amniotic membrane rupture by detection of the amniotic fluid diamine oxidase. The assay includes the steps of detecting the amniotic fluid diamine oxidase and distinguishing that from another form of diamine oxidase found in serum. The assay may be carried out on a sample of vaginal fluid from a pregnant female wherein the sample is subjected to the assay to detect the leakage or presence of amniotic fluid diamine oxidase. Purified forms of amniotic fluid diamine oxidase and serum diamine oxidase which is different from amniotic fluid diamine oxidase and found in serum are also described, together with a method of purifying both forms of diamine oxidase.

11 Claims, 14 Drawing Sheets

DIAMINE OXIDASE AND ASSAY FOR RUPTURE OF AMNIOTIC MEMBRANE IN PREGNANT MAMMALS

This is a continuation of PCT application No. PCT/AU90/00085, filed Mar. 2, 1990.

THIS INVENTION relates to purified forms of Diamine Oxidase (DAO) and in particular one form of this enzyme found in serum (hereinafter called serum DAO) and another form of this enzyme found in amniotic fluid (hereinafter called amniotic fluid DAO). The invention also relates to methods for preparation of these purified enzyme forms.

The invention also relates to an assay for detection of amniotic fluid DAO in body fluids and in particular to an assay for diagnosis of rupture of amniotic membrane or leakage of amniotic fluid through the membrane.

BACKGROUND OF THE INVENTION

Diamine Oxidase (E.C.1.4.3.6) (hereinafter called DAO) catalyses the oxidation of diamines such as histamine, putrescine and cadaverine, which yields an aminoaldehyde. During early investigations the enzyme was believed to only oxidise histamine: thus the enzyme was initially named Histaminase by Best and McHenry (1929). Further investigations proved that the enzyme was capable of oxidation of other diamines such as those listed above. The nomenclature currently in use, Diamine Oxidase, was later suggested by Zeller (1965).

Until 1965, the only intracellular mammalian diamine oxidase that had been purified was pig kidney histaminase (Kapeller-Adler, 1963; and Mondovi, 1964). Considerable purification of pig kidney histaminase (200- to 240-fold) was obtained by Tabor in 1951. Higher degrees of purification were successively obtained by applying column chromatography and electrophoresis (Mondovi, 1967a; and Uspenskaia, 1958). Diamine oxidase has also been purified from the pig kidney cortex by chromatography on hydroxylapatite and DEAE-Sephadex A-50, and gel filtration through Sephadex G-200 (Bardsley, 1971). This gave an enzyme preparation purified 230-fold with a 35% yield.

AH-Sepharose 4B was used as an affinity sorbent after partial purification of the pig kidney diamine oxidase by means of controlled heating, fractionation with ammonium sulphate and precipitation at pH 5.3. The AH-Sepharose adsorbed inactive proteins in preference to the diamine oxidase. This method provided an enzyme purified 670-fold, but with only a 14% yield (Floris, 1976). Increased yields of the enzyme from pig kidney was achieved by altering the heating conditions used by Floris (1976) on the homogenate, followed by ammonium sulphate fractionation and column chromatography on DEAE-Cellulose. Dialysis of the enzyme against 0.005M phosphate buffer resulted in an electrophoretically homogenous enzyme preparation purified 2400-fold with a 60% yield (Kluetz, 1977b).

Another method developed for purifying diamine oxidase from pig kidney cortex avoided heating the homogenate. The extract obtained after ammonium sulphate fractionation and centrifugation, was subjected consecutively to column chromatography on DEAE-Sephadex A-50 and hydroxylapatite, with subsequent gel filtration through Sephadex G-150. The enzyme was purified 1350-fold with a 20% yield, and was shown to be homogeneous by SDS-PAGE (Yamada, 1967). To simply the purification of pig kidney diamine oxidase, an affinity sorbent DAH-Sepharose was introduced by Klimova (1976). An extract of pig kidney cortex homogenate obtained after centrifugation of the ammonium sulphate treated sample was chromatographed on DAH-Sepharose and gave an enzyme preparation purified 200-fold with a 20% yield.

Human kidney diamine oxidase was purified 1800-fold by heating the homogenate, treating it with a mixture of ethanol and chloroform, chromatography on CM-Sephadex, and followed by fractionation with ammonium sulphate and gel filtration through Sephadex G-200 (Shindler, 1976).

Preparation of diamine oxidase from human placenta was achieved by fractionation with ammonium sulphate; chromatography on DEAE-Cellulose and phosphocellulose, and gel filtration through Sephadex G-200 (Smith, 1967). This preparation of diamine oxidase was purified 515-fold, although it still contained haptoglobin and methemoglobin. Paolucci (1971) obtained a 9600-fold purification of placental diamine oxidase with an 8% yield. The proteins of the human placenta were extracted using an acetone powder technique and precipitated with ethanol absorbed on DEAE-Cellulose; fractionated with ammonium sulphate, chromatographed on DEAE-Collulose and subjected to gel filtration through Biogel A-5m. A 4600-fold purification of human placental diamine oxidase was obtained by Bardsley (1974). The methods used in the purification of the enzyme were as those reported for Smith (1967), although a final chromatography step on DEAE-Sephadex or hydroxylapatite was employed which resulted in an increase in specific activity and gave an enzyme which was homogeneous by SDS-PAGE.

Hata (1976) obtained a 1200-fold purification of human placental diamine oxidase ontained by the method described by Bardsley (1974). The polyacrylamide gel electrophoresis pattern of purified human placental diamine oxidase gave a broad band, with the preparation not purified to the same extent as that described by Bardsley (1974). The purification of human placental diamine oxidase was also described by Crabbe (1976), using a modification of the procedure described by Bardsley (1974). Column chromatography incorporated DEAE-Sephadex with ionic strength and pH-gradient elution, together with affinity chromatography on Concavalin A-Sepharose. This gave a 30,800-fold purification with a 33% yield. Lin (1981) purified placental diamine oxidase in what was referred to as a one-step purification. In this procedure, placentae were homogenized and centrifuged, with the resultant supernatant applied to the affinity gel, cadaverine AH-Sepharose as was previously employed by Baylin (1975b). Elution of the enzyme was accomplished using chromotropic acid, and provided a 1800-fold purification of the enzyme which was homogeneous by SDS-gel electrophoresis.

Plasma diamine oxidase from women in the third trimester of pregnancy was purified 3000-fold with a 25% yield by means of an affinity sorbent sepharose, covalently linked with cadaverine (Baylin, 1975b). The enzyme was eluted from the adsorbent with heparin; electrophoresis by SDS-PAGE presented two protein fractions, one of which displayed the diamine oxidase activity.

Diamine oxidase was isolated from human female amniotic fluid by chromatography on DEAE-Sephadex and affinity chromatography on cadaverine-Sepharose, which was shown by SDS-PAGE to contain only 10% inactive protein (Tufvesson, 1978a). Diamine oxidase from human male serum previously given intravenous heparin (10000 I.U.) one hour before collecting the blood, was isolated by cadaverine-Sepharose affinity chromatography and then by chromatography on DEAE-Cellulose (Tufvesson, 1978b).

The enzyme can also be found in kidney and other organs in a variety of animal species. A great deal of time had been devoted to characterization studies of pig kidney (Kapeller-Adler & Macfarlane (1963)) and pig serum (Blaschko, Friedman, et al (1959)) DAO, but the human enzyme (Crabbe, (1979)) has been only poorly characterised.

According to previous studies, there seemed to be several forms of DAO and these forms exhibited some tissue specificity. Although presence of the enzyme in human placenta and human pregnancy plasma was confirmed by Swanberg (1950), this group was unable to establish any difference between the forms of human placental and pregnancy plasma DAO. Moreover, Tufvesson (1978) could find no difference between amniotic fluid DAO and pregnancy serum DAO, although he suggested that heparin stimulated male serum DAO was different.

Four active protein fractions, with molecular weights of 125,000, 250,000, 375,000 and 500,000 daltons were found in preparations of human placental diamine oxidase by Paolucci (1971). The preparation of human placental diamine oxidase obtained by Hata (1976) was purified 1200-fold, and the presence of a broad band on polyacrylamide gel electrophoresis indicated the presence of a contaminant protein which was demonstrated distinctly by immunoelectrophoresis and SDS-PAGE. The molecular weight was calculated to be approximately 300,000 by comparison with a calibration curve by gel filtration and SDS-PAGE. The molecular weight of the subunit was 170,000, which is about two times of 90,000 obtained by Bardsley (1974) and Lin (1981).

By the use of gel filtration through Sephadex G-200, polyacrylamide gel electrophoresis in the presence of SDS, or ultracentrifugation, it was demonstrated that a monomeric, catalytically active form of human placental diamine oxidase had a subunit molecular weight of 70,000 (Crabbe, 1976). This value is close to that reported by Baylin (1975b) for diamine oxidase from pregnancy plasma, which would appear to be a monomer. Sedimentation-equilibrium ultracentrifugation results indicated a single species with a molecular weight of 235,000, which could be explained on the basis of concentration-dependant-aggregation, to be dimeric and tetrameric species which were in equilibrium with each other (Crabbe 1976).

A protein component with a molecular weight of 185,000 was detected by means of gel filtration through Sepharose 6B on purified diamine oxidase from the serum of a man pretreated with heparin (Tufvesson, 1978b). However, a similar technique used on the serum diamine oxidase and amniotic fluid diamine oxidase of pregnant women revealed the presence of two active fractions in both which had native molecular weights of 245,000 and 485,000 (Tufvesson, 1978a, 1978b). Treatment of highly purified diamine oxidase from amniotic fluid with 1% SDS and 1% 2-mercaptoethanol followed by SDS-PAGE revealed the presence of a subunit with an apparent molecular weight of 100,000 dalton (Tufvesson, 1978a). Significantly, Tufvesson determined this apparent molecular weight in the presence of borate buffer which might be expected to lead to an overestimation of the subunit molecular weight. It is important to note here that Tufvesson did not determine the subunit molecular weight of his serum diamine oxidase preparation. Instead, he assumed that the pregnancy serum and amniotic fluid enzymes were identical presumably because of their identical apparent native molecular weights.

The isoelectric point of purified human amniotic fluid diamine oxidase was determined by measuring the activity of the bands which separated in two active fractions with pI values of 4.0 and 5.8. In considering the results for the isoelectric pH obtained for human placental diamine oxidase, Lin (1981) observed that the purified enzyme separated into 5 major bands and several diffuse bands, with the isoelectric pH of the major bands ranging from 5.3-6.6. In comparison, Crabbe (1976) determined the isoelectric point for human placental diamine oxidase to be 6.5. Thus, there is considerable confusion concerning the apparent isoelectric points of the various forms of diamine oxidase. It is highly likely that the observed isoelectric points are dependant on the method of purification or other factors because of the conflicting results of Lin (1981) and Crabbe (1976).

In respect to the several forms of DAO discussed above, it will be realised that pregnancy greatly modifies all metabolic patterns of histamine, putrescine and polyamines. Histamine and putrescine are produced in large amounts by the fetus. The level of DAO rises in parallel with the levels of histamine and putrescine during pregnancy (Zeller above). During a normal pregnancy the level of DAO in maternal plasma begins to rise from the second to third month reaching a maximum by the fifth to seventh month and remains at this level until parturition. The level of DAO in plasma falls quite rapidly after parturition (Lorenz, Kusche, 1970). The major function of DAO during pregnancy appears to be to ensure that the levels of the biogenic amines in the placental microcirculation do not become elevated and thus toxic to the developing fetus (Buffoni, 1966).

Premature rupture of the fetal membranes was observed in 6-16% of all pregnancies (Swartz, Napolitani, et al 1969), while another study found the rupture of fetal membranes in 3-14% of all pregnancies was not followed by labour (Larsen, 1979). On rupture of the membranes, Eastman & Hellman (1961) observed that spontaneous labour followed within 24 hours in 80% of patients, with 10% remaining undelivered after a period of 48 hours. The perinatal mortality doubles after a latent period of 24 hours and again after 48 hours (Overstreet and Romney, 1966). Delayed onset of labour carries with it an increased risk of maternal and perinatal infection and mortality (Eastman & Hellman; Kapeller-Adler & Macfarlane; Overstreet above), therefore the accurate detection of ruptured membranes is an important diagnostic aid.

In the mature fetus therefore, early diagnosis of membrane rupture allows for expediting the delivery thereby reducing infection risk to mother and baby. In the premature infant, accurate diagnosis of membrane rupture is even more important particularly if labour needs to be induced. A reliable, easy method of diagnosis of membrane rupture would be clinically useful to the obstetrician and also cost saving by reducing the need for prolonged and unnecessary hospitalisation. The benefit to those patients resident in the country areas and facing transfer to a tertiary care centre for prolonged periods of hospitalisation away from home and family environment on suspicion of having premature rupture of the membranes would be considerable.

High concentrations of DAO found in amniotic fluid are almost equal to that of maternal blood plasma (Tornqvist, 1971). After rupture of the membranes, DAO is demonstrable in the vagina; wherefore in absence of vaginal bleeding or exudation the measurement of the DAO content of vaginal fluid has been shown to be a reliable method in evaluation of membrane rupture (Ahlmark, 1944); Elmfors, Tryding, et al (1974); Gahl, Kozina, et al (1982). Besides physical examination, current techniques for establishing the diagnosis of ruptured fetal membranes are (Elmfors, Tryding (1976))
1. Determination of the vaginal pH;
2. Staining for fetal fat globules;
3. Identification of fetal squamous cells or hairs;
4. Examination for typical crystallisation of amniotic fluid (ferming).

In accordance with Friedman and McElin (1976) any three of the abovementioned methods taken together provide an accuracy of 93% although false-positive and false-negative results are frequent with all laboratory techniques which are applied in diagnosing rupture of the membranes (Larsen above). Dyes and other chemicals have been injected into the amniotic fluid transabdominally and their appearance looked for in the vagina but these techniques are not without risk (Jimsenez-Balderaz E. A. Bol. Med. Hosp. Infant Mex. 1984, 41, P341-4). Measurement of amniotic fluid volume by ultrasound before and after bed rest may be helpful but is not specific (Rudd above).

Measurements of the protein alpha-fetoprotein and the hormones prolactin and human placental lactogen have been investigated by Huber, J. F. et al (Huber, J. F. et al, Are Vaginal Fluid Concentrations of Prolactin, alpha-Fetoprotein and Human Placental Lactogen Useful for Diagnosing Ruptured Membranes, Br. J. Obstet. Gynacol. 90, 1183-1185) but he found many positive tests in patients whose membranes were intact. This was due in part to the fact that these substances are present in maternal serum and therefore the test is positive when either serum or amniotic fluid or both are present in the vagina.

Rochelson B. C. (Rochelson, B. C., A rapid colorimetric AFP monoclonal antibody test for the diagnosis of preterm rupture of the membranes. Obstet, Gynaecol, 1987, 69, P163-6) has also found blood and serum to give false positive results with his test for the presence of alphafetaprotein in vaginal fluid). Elmfors et al (above), using the information of Tornqvist & Jonassen (above) developed a method for the diagnosis of ruptured membranes by measuring the DAO activity in vaginal fluid. DAO activity is present in amniotic fluid but normally absent from vaginal secretions, presenting a method for diagnosing rupture of the membrane (Elmfors, Tryding et al above; Gahl, Kozina, et al above). The most widely used method for collection of DAO activity in vaginal secretions is the use of blotting paper to collect the secretions and phosphate buffer to elute the enzyme (Elmfors, Tryding above). Wishart, Jenkins et al (1979) also supported the use of the procedure and found an assay to offer useful clinical information. The factors which suggest that the DAO assay may be used as an adjunct to conventional tests in the diagnosis of rupture of membranes have been summarised by Gahl et al (above). However, the major drawback of the assay is that it depends on the measurement of enzyme activity and can give false results in the presence of interfering substances such as:
1. urine;
2. meoonium;
3. antiseptics;
4. pregnancy serum;
5. seminal fluid;
6. haemoglobin These substances commonly contaminate the vagina therefore invalidating current methods which are limited by interfering substances, inadequate sensitivity and subjective interpretation of results.

DESCRIPTION OF THE INVENTION

It is therefore an object of the present invention to provide an assay for diagnosis of amniotic membrane rupture or leakage of amniotic fluid which is reliable and alleviates the problems encountered in the prior art assays above.

The invention therefore provides an assay for the detection of amniotic fluid in body fluids and in particular an assay for diagnosis of rupture of the amniotic membranes in pregnant mammals or leakage of amniotic fluid and in particular pregnant women including the step of detecting the presence of amniotic fluid DAO in vaginal fluid and distinguishing same from serum DAO.

In regard to pregnancy in females inflammation of the birth canal and in particular the cervix may cause leakage of maternal serum into the vagina. Maternal serum contains serum DAO and it has now been surprisingly discovered by the process of the present invention that serum DAO may be differentiated from amniotic fluid DAO by appropriate techniques described in detail hereinafter.

When rupture of the amniotic membrane occurs this causes leakage of amniotic fluid into the vagina with the subsequent result that the vagina will contain amniotic fluid DAO. It is thus evident that if the presence of amniotic fluid DAO may be detected and distinguished from serum DAO then a valuable tool will be provided for early diagnosis of amniotic membrane rupture. This therefore provides a clear demonstration that "breaking of the waters" has occurred and thus false alarms caused by vaginal fluid leakage may be avoided. False alarms are particularly prevalent when vaginal fluid may be leaked or emitted from the vagina after swimming or taking a bath.

It is believed following the development of the present invention that amniotic fluid DAO (hereinafter AF-DAO) is a modified form of serum DAO (hereinafter S-DAO) and that for example AF-DAO may have a surrounding envelope of polysaccharide or amide or alternatively may have a different biological conformation. it is also possible that AF-DAO may comprise S-DAO with a component removed therefrom or added thereto. In any event the present invention is not bound by any particular theory and is solely based on the discovery that S-DAO is indeed a different protein when compared to AF-DAO. This therefore means that S-DAO may be differentiated from AF-DAO by appropriate techniques which include differences in subunit molecular weight or biological activity. However probably the best method of distinguishing between AF-DAO and S-DAO is by the use of immunological techniques such as RIA, FIA, EIA, ELISA, agglutination including latex beads or chemiluminescence. In this regard therefore development of an appropriate antibody which may be polyclonal or monoclonal in nature would be of assistance in distinguishing S-DAO from AF-DAO. Thus a specific polyclonal or monoclonal antibody for either S-DAO or more probably AF-DAO will be extremely useful in differentiating these proteins.

The present invention therefore can be utilised in the following cases:

(i) where there is premature rupture of the amniotic membrane without blood loss;

(ii) where there is premature rupture of the amniotic membrane with blood loss;

(iii) where there is a lesion of the birth canal and particularly the cervix without rupture of the amniotic membrane;

(iv) where there is no rupture of the amniotic membrane and no lesion; and (v) where there is rupture as well as a lesion.

In the case of (i) above a test for presence of AF-DAO in the vaginal fluid would be positive and a test for S-DAO would be negative.

In the case of (ii) above tests for AF-DAO and S-DAO would both be positive.

In the case of (iii) above a test for AF-DAO would be negative and for S-DAO would be positive.

In the case of (iv) above both tests would be negative.

In the case of (v) above both tests would be positive.

It is therefore within the scope of the present invention that diagnosis of one or all of the above cases (i) to (v) are contemplated.

The assay of the invention in a preferred form may include the following steps:

(a) obtaining a sample of vaginal fluid from a pregnant female;

(b) reacting the sample with antibody derived from S-DAO or AF-DAO; and (c) detection of reactivity by a signal amplification.

The invention may also include within its scope a test system or kit for use with the method described above. this may include S-DAO and/or AF-DAO antibody which is immobilised to an inert surface such as a test tube or other suitable vessel. The antibody which is suitably a monoclonal antibody may be physically or chemically bound to the inert surface.

However, more suitably, the reaction system may include an immunoabsorbed polyclonal antibody for S-DAO and/or AF-DAO immobilised to the inert surface. A further component of the reaction system may be a tag polyclonal or monoclonal antibody for S-DAO and/or AF-DAO which has a suitable label attached thereto. Upon reaction with AF-DAO or S-DAO with the polyclonal antibody the tag monoclonal antibody may be bound to the AF-DAO or S-DAO antigen and the label subsequently detected by any suitable means as described above. Thus if the label is an enzyme a suitable enzyme substrate may be used. Alternatively RIA, FIA, agglutination chemiluminescence or a dipstick detection may be used depending upon the label.

In regard to the foregoing it will also be appreciated that the term "rupture" may also include within its scope a perforation of the amniotic membrane which does not need to complete rupture or breakdown thereof. In some cases a perforation could well exist in the amniotic membrane resulting in leakage of amniotic fluid but without resulting in complete rupture or breakdown of the membrane.

In another aspect of the invention, there is also provided two forms of DAO that have now been characterized by a variety of physico-chemical methods and that these physico-chemical methods may be used to clearly differentiate between these forms.

One form of DAO located in serum has now been characterized by possessing the following physical properties:

(i) a subunit molecular weight of approximately 75,000 daltons performed by SDS-PAGE with gels of different acrylamide concentrations;

(ii) a native molecular weight analysis determined by gradient-PAGE or gel filtration chromotography and which revealed a number of species having apparent molecular weights of approximately 120,000; 160,000 and 480,000 respectively.

(iii) isolectric focusing studies revealed a pattern characteristic of a glycoprotein and with substantive bands with isoelectric points greater than 5.

(iv) analysis of the purified enzyme by electrophoresis on agarose gels and immunofixation with polyclonal antisera revealed multiple bands of activity different to these bands corresponding to amniotic fluid DAO; and (v) immunoadsorption of the polyclonal antisera raised to amniotic fluid DAO with maternal serum and purified maternal serum removed all reactivity to the maternal serum proteins when tested by immunofixation.

Another form of DAO located in amniotic fluid has also been characterized by possessing the following physical properties:

(i) a molecular weight of approximately 79,000 daltons performed by SDS-PAGE with gels of different acrylamide concentrations (When this preparation was compared with maternal serum DAO on the same plate, it consistently showed a higher apparent subunit molecular weight by approximately 4,000 daltons);

(ii) a native molecular weight analysis as determined by gradient-PAGE or gel filtration chromatography and which revealed a number of species having apparent molecular weights of 120,000; 160,000 and 480,000 daltons. These values are the same as observed for pregnancy serum DAO. The differences between these values and those obtained by Tufvesson (1978b) can be explained by the presence of an impurity (monoamine oxidase) in his preparation;

(iii) isolectric focusing studies revealed a pattern characteristic of glycoproteins with bands observed having isoelectric points mainly below 5.0;

(iv) analysis of the purified enzyme by electrophoresis on agarose gels and immunofixation with polyclonal antiserum revealed multiple bands of activity different to those bands corresponding to serum DAO; and (v) immunoadsorption of the polyclonal antiserum raised to amniotic fluid DAO with maternal serum and purified material serum DAO removed all reactivity to the maternal serum proteins when tested by immunofixation but retained activity to amniotic fluid diamine oxidase.

From the foregoing it will also be appreciated that the invention includes within its scope a method of purification of serum-DAO or AF-DAO wherein serum DAO may be obtained from a suitable source of pregnant serum and AF-DAO obtained from a suitable source of amniotic fluid.

The serum DAO and AF-DAO may be purified using any suitable method of protein purification such as ion exchange chromatography, gel filtration chromatography, electrophoresis, immunoabsorption, affinity chromatography, electroelution or hydroxylapatite chromatography. However, a preferred purification method includes the following steps:

(i) passing a preparation of serum-DAO and AF-DAO through a first column capable of binding glycoproteins or proteins having associated therewith carbohydrate groups;

(ii) eluting the bound preparation of AF-DAO and Serum-DAO from the column;

(iii) passing the preparation of Serum-DAO and AF-DAO through a second column having binder or ligand which binds to active sites of AF-DAO and Serum-DAO; and (iv) eluting the AF-DAO and Serum-DAO from the second column.

In step (i) above the first column may comprise an inert support such as Sepharose (eg Sepharose 4B or Sepharose 6 MB) having attached thereto a ligand such as lectins which are plant proteins having high affinity for sugar resides. Suitable examples are concavalin A and wheat germ agglutinin. Concavalin A binds to internal and non reducing terminal alpha-mannosyl resides whereas wheat germ agglutinin binds to terminal N-acetylglucosamine residues.

Particularly preferred inert support ligand combinations are lentil lectin Sepharose 4B and wheat germ lectin Sepharose 6 MB.

The starting material which required purification by the abovementioned process may be obtained from pregnancy serum or amniotic fluid as described above and may suitably include a filtration or dialysis step or both before being passed through the first column.

Suitable eluants that may be used in step (ii) included carbohydrate molecules or sugars or sugar derivatives such as glucosides and mannosides. Suitable examples are alpha-D-methyl mannoside, alpha-D-methyl glucoside, mannose or glucose.

In step (iii) the second column suitably includes an inert support such as Sepharose having attached thereto a ligand which has a terminal free amino group. This is necessary to bind to active sites of the Serum-DAO or AF-DAO so as to form an $NH_2$ grouping whereby the ligand is bound to the enzyme by electrostatic attraction. Suitable ligands are those bearing the general formula $NH_2-(CH_2)_n-NH_2$ wherein n is 1 to 8. Suitable compounds falling within the scope of this formula are cadaverine (n=5), putrescine (n=4) and hexanediamine (n=6).

Suitable eluants that may be utilized in step (iv) include salts of concentrations to IM (e.g. 0.2% NaCl) or heparin. Heparin is preferred because it does not having a denaturing effect as is the case with some salts.

Estimation of the subunit molecular weight of both the AF-DAO and S-DaO is suitably carried out electrophoretically using sodium dodecyl sulphate (SDS) and mercaptoethanol. The latter reagent or any other suitable reagent may be used to break any disulphide bridges occurring in the proteins and SDS or other suitable reagent is used to bind to the protein in nonpolar sections thereof so that the molecule has a net overall electric charge suitable for migration in an electric field.

EXPERIMENTAL

DAO was purified by the process of affinity chromatography and gel filtration. All chromatographic procedures were performed at 2°-8° C. unless stated otherwise.

Initially the whole serum and amniotic fluid were passed through glass wool; filtered fractions were then applied onto a Con-A-Sepharose column (Pharmacia, Cat. No. 17-0440-01); equilibrated with the wash buffer as follows:
20 mM Tris/HCl, pH 7.4
0.5M NaCl
1 mM $MnCl_2$
1 mM $CaCl_2$ Filtered amniotic fluid or serum were loaded onto the Con-A-column and contaminant proteins eluted with the wash buffer. The bound protein fraction was eluted with the following buffer system;
50 mM alpha-methyl-D-glucoside
(SIGMA, Cat No. M 1379)
20 mM Tris/HCl, Ph 7.4

Activity of the fractions was determined with fractions displaying the highest activity being pooled. DAO activity was measured by the modified procedure of Gahl et al (1982). The activity was determined by incubating 0.5 ml of eluate with 0.1 ml of (14 C) putrescine dihydrochloride (109 mci/mmol, Amersham Laboratories, Code CFA. 301) in 1.5 ml of 1/15M phosphate buffer (pH7.6). The reaction mixture was incubated for 30 minutes at 55° C., after which the reaction was terminated by the addition of 0.2 ml 10 mM guanidine hydrochoride (Sigma; Cat. No. 64505). To the reaction mixture, 10 ml of scintillation grade Toluene (Packard; Cat. No. 6013909) containing 0.5% Butyl-PBD (Packard; Cat. No. 6002154) was added; the cocktail shaken for 10-15 min. then placed into −70° C. for 30 min. Blanks were run either with buffer alone or with maternal serum and amniotic fluid in the presence of 10 mM guanidine hydrochloride. The organic phase was transferred to new scintillation vials and counted on the LKB Rack Beta. The second state of purification was based upon the binding of DAO to the substrate cadaverine (SIGMA Cat. No. C8382), which was coupled to CH-Sepharose-4B (Pharmacia, Cat. No. 17-0460-01) using the coupling reagent carbodiimide (SIGMA, Cat. No. E6383). Contaminant proteins were eluted from the column with the following buffer system:
0.2M NaCl
20 mM Tris/HCl, pH 7.4

DAO was consequently eluted from the column with Heparin; 1000 Units/ml (Commonwealth Serum Laboratories). Fractions with the highest activity were pooled and concentrated against 20 mM Tris/HCl pH 7.4 using Amicon concentrators (Amicon, Prod. No. 4208). Concentrated fractions were stored at −70° C. in the presence of glycerol (40% v/v).

Electrophoresis was performed in the presence of SDS (SIGMA Cat. No. L4509) and 2-Mercaptoethanol (Biorad, Cat. No. 161-0710) by the method described by Laemmli (1970).

Gels were prepared from the following stock solutions: 29.2 g acrylamide (Gradipore, Prod. No. RE-100) and 0.8 g Bis (Gradipore, Prod. No. RE-180) in a total volume of 100 mls. This solution was filtered through Whatmans No. 1 and stored at 20°-25° C. in the dark. The buffers used in making the gels are as follows: The resolving gel was composed of 1.5M Tris/HCl, pH 8.8 and the stacking buffer was 0.5M Tris/HCl, Ph 6.8. The sample buffer consisted of the following:
12.5%(v/v) 0.5M Tris/HCl pH 6.8
10%(v/v) Glycerol
20%(v/v) of 10%(w/v) SDS
5%(v/v) 2-Beta-Mercaptoethanol
2.5%(v/v) of 0.05%(w/v)

Bromophenol blue
50% distilled water

Proteins were diluted ⅛ to ¼ with sample buffer and heated at 95° C. for 5-10 minutes.

The standard proteins were obtained from Pharmacia (Low molecular weight calibration kit, Cat. No. 17-0442-010).

The subunit molecular weights of serum and amniotic fluid DAO were determined by comparing their mobilities on gels with the protein standards.

Serum DAO and amniotic fluid DAO were also purified by the process of affinity chromatography as previously described by Klimova et al (1976). The procedure was based upon the binding of DAO to 1,6-hexanediamine (Pharmacia; Cat. No. H2381), a diamine substrate for DAO, which was coupled to Sepharose 4B (Pharmacia; Cat. No. C1150) via the spacer arm adipic dihydrazide (Pharmacia; Cat. No. A0368). Prior to column application, samples of amniotic fluid and maternal serum were dialysed for 2 hours against two changes of 0.01M phosphate buffer (pH 7.6) followed by two changes of distilled water. Contaminant proteins were removed from the column with 0.01M phosphate buffer (pH 7.6); amniotic fluid DAO was eluted with 1.0N NaCl, and serum DAO eluted with 1.0N NaCl and 0.2M phosphate buffer (pH 7.6). All chromatographic procedures were performed at 4° C. DAO activity was measured by the procedure of Gahl et al (1982) as described previously. Samples with the highest activity were pooled and dialysed against three changes of 0.01M phosphate buffer (pH7.6) then three changes of distilled water over a period of 2 hours. Upon completion of dialysis, dialysed samples were lyophilised and resuspended to a concentration of 10 g/l prior to electrophoresis.

Protein estimations were performed during each stage of purification using the Bio-Rad Protein Assay (Cat. No. 500-0001).

Protein electrophoresis was performed on Titan gels (Helena Laboratories; Cat. No. 3046) and Beckman Paragon gels (Lot No. M70 7019). Protein solutions of 2-5 ul were applied to the gel and electrophoresed at 100 V for 30 min. on Beckman plates; and at 250 V for 22-25 min. on Titan gels. Protein migration on Titan gels was observed by adding bromophenl blue (BDH Chemicals; Prod. No. 20015) to the amniotic fluid or maternal serum sample. Upon completion of electrophoresis, the gel was removed and placed into 10% picric acid solution for 10-15 min. Gels were air-dried, stained in Coomassie Brilliant Blue R-250 (Bio RAD; Cat. No. 161-0406) destained and dried at 60 degrees C. The destaining solution consisted of glacial acetic acid, methanol and distilled water in the ratio of 1:1:8.

Measurement of protein activity was performed on completion of electrophoresis; gel slices of 3×5 mm were removed and suspended in 0.01M phosphate buffer (pH7.6). The gel strips were incubated for a period of 1 hr at 37 degrees C. then for 24 hrs at 4 degrees C., following which the activity was measured by the procedure described above.

Guinea pig antihuman amniotic fluid DAO was prepared by subcutaneously injecting a mixture of amniotic fluid DAO (0.1 mg/ml) and Freund's "complete" adjuvant (Commonwealth Serum Laboratories) in a ratio of 1:1. The booster injections utilised Freund's "incomplete" adjuvant, the first was given at 6 weeks, the second at 9 weeks. Blood was collected from the ear veins and the titre of the antisera was tested at 9 weeks.

At 16 weeks 3-5 ml of blood was collected by cardiac puncture from one guinea pig. One guinea pig was sacrificed so that 10-15 ml of blood was collected. Adsorption of nonspecific antisera was performed by treating the antiserum with serum DAO and maternal serum in the ratio 50:3:1. The treated antiserum was incubated at 37 degrees C for 1 hr then at 4 degrees C for 10 days. Once centrifuged, the immunoadsorbed supernatant was stored at −70 degrees C until required. The specificity of the antiserum was further tested by performing immunofixation against maternal serum, human amniotic fluid and purified maternal serum DAO.

| ISOELECTRIC FOCUSING | |
|---|---|
| Reagents | |
| Pharmalyte (3-10) | (PHARMACIA) |
| Servalyte (4-9) | (SERVA) |
| Gelbond | (FMC) |
| Gel Suspension | |
| 0.3 g Agarose IEF | (PHARMACIA) |
| 3.0 g Sucrose | (AJAX) |
| 27.0 ml Distilled water | |
| Gel Fixative | |
| 5% Sulphosalicylic acid | (AJAX) |
| 10% Trichloroacetic acid (TCA) | (BDH) |
| Staining Solution | |
| 0.25% Coomassie Brilliant Blue R-250 | |
| Prepare the dye in destaining solution | |
| and filter through Whatman no. 1 filter | |
| paper before use. | |
| Destaining Solution | |
| 30% Methanol | |
| 10% Acetic acid | |
| pI Calibration Kits | |
| Low pI Calibration kit (2.5-6.5) | (PHARMACIA) |
| Broad pI Calibration kit (3-10) | (PHARMACIA) |
| Electrode Buffers | |
| Anode buffer: 0.05 M Sulfuric acid ($H_2SO_4$) | (BDH) |
| Cathode buffer: 1 M NaOH | |
| Electrode buffer strips | (PHARMACIA) |

Procedure for Isoelectric Focusing

The LKB Multiphor IEF system was utilized for all electrofocusing studies. Agarose gels were prepared with ampholines to give pH ranges of 4-9 and 3-10 respectively. Agarose gels were prepared on gelbond which was clamped with the casting mould onto the levelling plate; the gelbond was pre-heated using a hair drier prior to the application of the gel suspension. Before addition of ampholines, the gel suspension was heated under a gas flame untial all components had dissolved; the temperature of the suspension was monitored and the ampholines added to the mixture once the temperature had fallen to 75° C. The gel suspension was poured onto the pre-heated casting tray and the bubbles removed with a syringe needle. The gels were allowed to polymerize at R.T. for 30-40 min then stored at 4° C. for a minimum period of 1 hr before use. The cast gel was placed onto the cooling plate (pre-cooled to 9° C.) with an even thin film of water separating the gel and cooling plate. The electrode strips were firstly blotted on filter paper to remove excess moisture, then applied onto the gel and pressed along their entire surface to ensure proper contact with the gel surface. The electrofocusing lid was connected, ensuring proper contact between the electrodes and buffer strips, and the gel was pre-focused for 20 min at 1500 V, 5 W, 150 mA. Upon completion of pre-focusing, Samples were applied to the gel surface into the wells of the plastic sample template (PHARMACIA). Volumes of 10-25 ul were applied for both the protein samples and pI markers (reconstituted in 0.1 ml of distilled water). The electrofocusing lid was re-connected and the samples allowed to move into the gel at 1500 V, 5 W, 150 mA for 20 min. The electrofusing lid was removed, the template was blotted with filter paper and removed; the samples were then further focused for a period of 1 hr at 1500 V, 10 W, 150 mA. Upon completion of focusing, the gel was immediately placed into fixative for 30 min, followed by 2×30 min washes in destaining solution. The gel was then dried by placing filter paper onto the gel and glass plates as weights for 30 min; the gel was then dried to completion using a hair drier. The gel film was then placed into staining solution for 10-15 min then destained until a clear background was achieved. Finally, the gel was dried with a hair drier for a permanent recording of the gel.

| AGAROSE GEL ELECTROPHORESIS | |
|---|---|
| Agarose Gels | |
| Beckman Paragon IFE Gels | (BECKMAN) |
| Agarose | (LKB) |
| Barbital Buffer | |
| 15 g Barbituric acid | (BDH) |
| 47.5 g Sodium barbitone | (BDH) |
| 23 g Tris | |

Dissolve barbituric acid and sodium barbitone in 1.0 l of boiling distilled water. Add tris and adjust volume to 4.0 l; adjust pH to 8.8 with 1M HCl.

Procedure for Agarose Gel Electrophoresis

Agarose gels were prepared by adding agarose powder (1% w/v) to barbital buffer and boiling the solution on a hot plate; the solution was mixed until the agarose had dissolved. The agarose was then cooled (to approximately 0° C.) and poured into a 10 ml syringe with a 16-gauge needle and applied to the gel casting assembly (pre-heated at 55° C.) which consisted of 10×10 cm glass plates separated by a 0.5 mm spacer and Gelbond. The gel was allowed to set at 4° C. for 1 hr prior to use. Proteins samples of 3-5 µl were applied to the gel surface with the aid of a template. Bromophenol blue prepared in distilled water (0.1%) was added to samples of maternal serum or amniotic fluid as a marker. Electrophoresis was performed using the beckman Electrophoresis System and the Zip-Zone electrophoresis chamber and cooling plate (HELENA). Proteins were electrophoresed for 30 min at 100 V constant voltage using the 2103 Power Supply (LKB). Upon completion of electrophoresis, proteins were fixed in 50% methanol, 10% acetic acid for 30 min. The gel was then dried with a hair drier and stained according to the IEF staining procedure discussed herein.

Activity Studies Performed With Agarose Gels

Following the completion of protein electrophoresis on the agarose gel, sections of the gel of 3×5 mm were removed with a scalpel and placed into a 5 ml glass test-tube. The gel sections were incubated in the presence of 0.5 ml of 1/15M sodium phosphate buffer, pH 7.4, for a period of 7 days at 4° C. The enzyme activity of each section was then measured by radioenzymatic analysis of the sample buffer.

IMMUNOFIXATION

Immunofixation was performed on agarose gels using guinea pig anti-human amniotic fluid DAO antisera. All antisera were immunoadsorbed with maternal serum and purified maternal serum DAL; the mixture was incubated in an eppendorf tube for 1 hr at 37° C. then incubated at 4° C. for 1 week. The antisera were centrifuged for 10 min at 5000 g in a Beckman Centrifuge; the supernatant was collected and stored at −70° C. in 0.1-0.2 ml aliquots. Proteins were electrophoresced on agarose gels as previously described prior to immunofixation. Upon completion of electrophoresis, both immunoadsorbed and non-adsorbed antisera were applied to cellulose acetate strips which were then placed onto the gel surface corresponding to the area of protein electrophoresis. The gels were then incubated at R.T. for 1 hr in a humidity chamber; the cellulose acetate strips were removed and the gel was put through the wash and dry process. This process involved washing the gel for 3×15 min cycles in saline, then drying the gel after each wash cycle for 10-15 min by placing filter paper and a 500 g weight onto the gel. On completion of the third saline wash, the gel was completely dried with a hair drier and stained as previously described for agarose gels. For a direct comparison of the immunofixation to the protein patterns, the outer tracks of the agarose gel were cut out and stained for proteins.

IMMUNOPRECIPITATION

To access the extent DAO activity was removed from maternal serum and amniotic fluid by antibody the fluids were incubated with different volumes of polyclonal antisera. To 0.5 ml of amniotic fluid and maternal serum, 0.01-0.1 ml of the antibody was added and incubated for 2 hr at 37° C. in eppendorf tubes. Control tubes were also prepared with 0.01-0.1 ml of 1/15M phosphate buffer pH 7.4 supplemented for the antibody. The tubes were then centrifuged at 5000 g for 10 min on a Beckman Centrifuge and the supernatants collected and tested for enzyme activity by radioenzymatic analysis.

Using the procedures previously described to purify DAO (affinity sorbent DAH-Sepharose as introduced by Klimora and co-workers 1976) resulted in an approximately 11-fold purification for amniotic fluid DAO (Table 1) and a 32-fold purification for maternal serum DAO (Table 2). To examine the effect of phosphate buffer on DAO activity, different concentrations of the phosphate salts were introduced to the radioenzymatic procedure to observe their effect on DAO activity. The results displayed in FIG. 1 show that in the presence of increasing levels of phosphate, there is a considerable loss in enzyme activity. There is an approximate 20% loss in DAO activity in amniotic fluid and maternal serum when incubated in the presence of 0.2M phosphate buffer (elution buffer for DAH-Sepharose affinity chromatography).

Tables 3 and 4 represent the various stages of DAO purification from maternal serum and amniotic fluid using the second purification procedure.

The first stage of this purification process utilized the properties of A-Sepharose, enabling it to bind glycoproteins. In particular, to isolate the carbohydrate containing components from whole serum and amniotic fluid prior to further purification processes. Pool fractions of both fluids were applied to Con A-Sepharose and the contaminated proteins washed through the column; no DAO activity was observed in the wash fraction as determined by radioenzymatic analysis. Elution of the fraction containing DAO activity was performed using the glycoside methyl-D-glucosidase. The enzyme activity was eluted in a broad elution peak with poor recovery of the activity; approximately 2.2% for amniotic fluid and 2.7% for maternal serum. Those fractions demonstrating the highest activity were pooled, concentrated and loaded on the Cadaverine-Sepharose column. Contaminant proteins were removed from the Cadaverine-Sepharose column with the equilibration buffer; radioenzymatic analysis of the contaminant fractions revealed no DAO activity. The elution of the DAO fraction was performed with 20 mM Tris 1M NaCl which resulted in the elution of a well defined peak. The results of the radioenzymatic assay revealed that the extent of enzymatic activity recovered was approximately 30% for amniotic fluid and 55% for maternal serum. The purification of amniotic fluid and maternal serum post Cadaverine-Sepharose affinity chromatography had resulted in a considerable loss in enzyme activity, the causative factor of which was believed to be the high salt concentration of the elution buffer. To examine the effect of salt on DAO activity, an experiment was performed incorporating varying concentrations of NaCl in 1/15M phosphate buffer for the radioenzymatic assay, and observing the outcome of the DAO activity in maternal serum and amniotic fluid. In observing the salt effect on DAO (FIG. 2), an increase in the level of salt present in the buffer had a considerable effect on the activity of the enzyme; with an approximate loss of 80% for both amniotic fluid and maternal serum DAO in the presence of 1M NaCl. The removal of the salt by dialysis or with the stirred cell allowed on an average for 10% recovery in enzyme activity, with an overall loss of 70% for both fluid proteins. To eliminate the use of salt in the elution buffer, heparin was substituted for NaCl to elute DAO from the Cadaverine-Sepharose affinity column. Upon removal of the contaminant proteins with the wash buffer, a step-wise gradient of elution buffer containing 100–1000 Units of heparin was introduced to the affinity column. Radioenzymatic analysis of the fractions collected from the heparin elution confirmed that the DAO activity was confined to the peak resulting from the elution with 1000 U of heparin. The addition of the elution buffer with 1M NaCl to the affinity column after heparin elution, resulted in no further elution of DAO activity, although a small contaminant protein peak was observed. The results for the recovery of enzyme activity revealed an approximate level of 21% for amniotic fluid (Table 5) and 14% for maternal/serum (Table 6).

Tables 5 and 6

The presence of heparin, as was determined by the radioenzymatic assay; had no effect on the overall enzyme activity when incubated in the presence of amniotic fluid and maternal serum. To evaluate the extend of protein loss due to the membranes in the stirred cells, purified amniotic fluid and maternal serum DAO were diluted in 20 mM Tris (pH 7.4) and the enzyme activity was determined both prior to and following sample concentration. The results revealed on average a 8% loss in enzyme activity due to probable protein retention.

ELECTROPHORESIS

Figure 3:
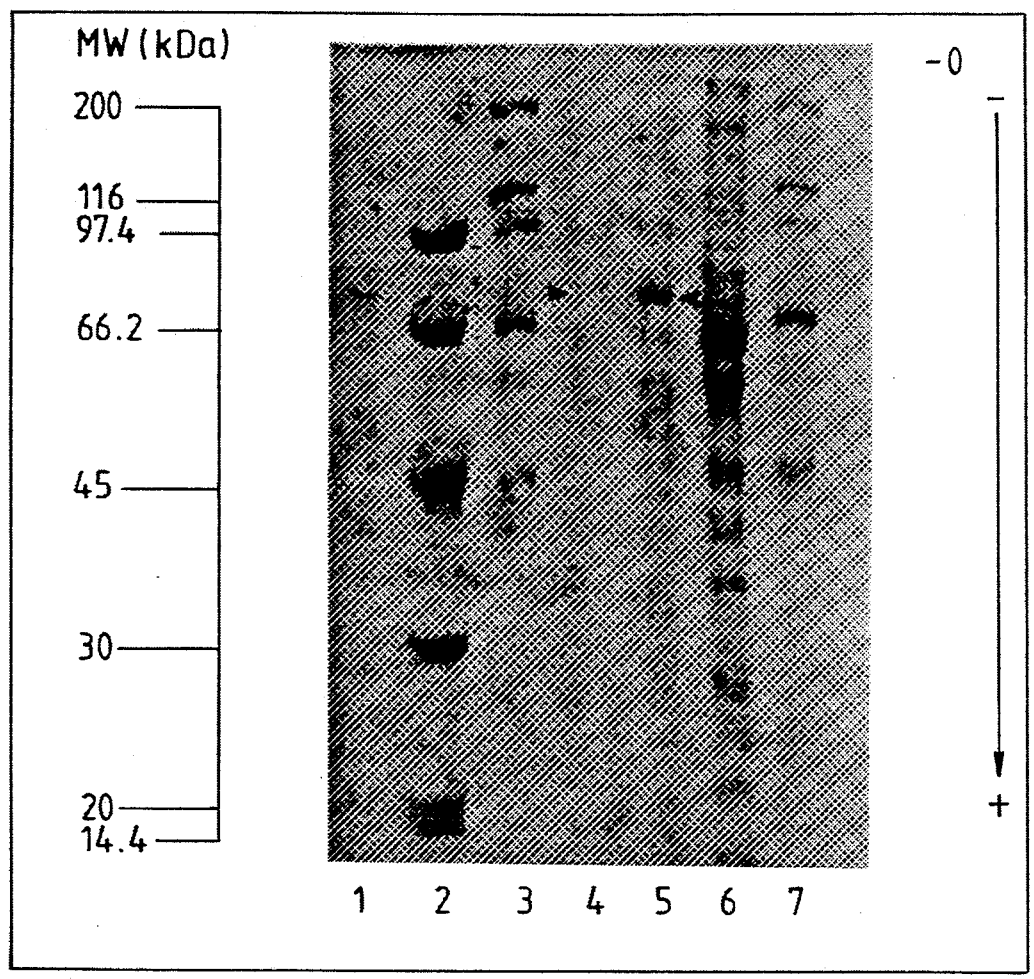

FIG. 3 shows the electrophoretic patterns on a 10% SDS polyacrylamide gel of purified amniotic fluid and maternal serum DAO eluted with 1M NaCl from the Cadaverine-Sepharose affinity column. This was compared to maternal serum DAO purified by DAH-Sepharose affinity chromatography. The subunit molecular weight estimated from the calibration curve constructed by plotting the log M.W. against protein migration, was determined to be approximately 79,000 for amniotic fluid DAO and 75,000 for maternal serum DAO. A comparison by SDS-PAGE of DAO purified by DAH-Sepharose revealed a number of contaminant proteins; moreso than when compared to the amniotic fluid and maternal serum DAO purified by Cadaverine-Sepharose affinity chromatography and eluted with 1M NaCl. A high molecular weight contaminant was present in the purified preparations of amniotic fluid and maternal serum from Cadaverine-Sepharose chromatography. Comparison with the purified fractions of DAO from DAH-Sepharose chromatography revealed a greater degree of contamination, moreso for maternal serum DAO (FIG. 3). The contaminant proteins were removed by the process of gel-filtration HPLC, no enzyme activity was observed in the contaminant fractions.

Figure 4:
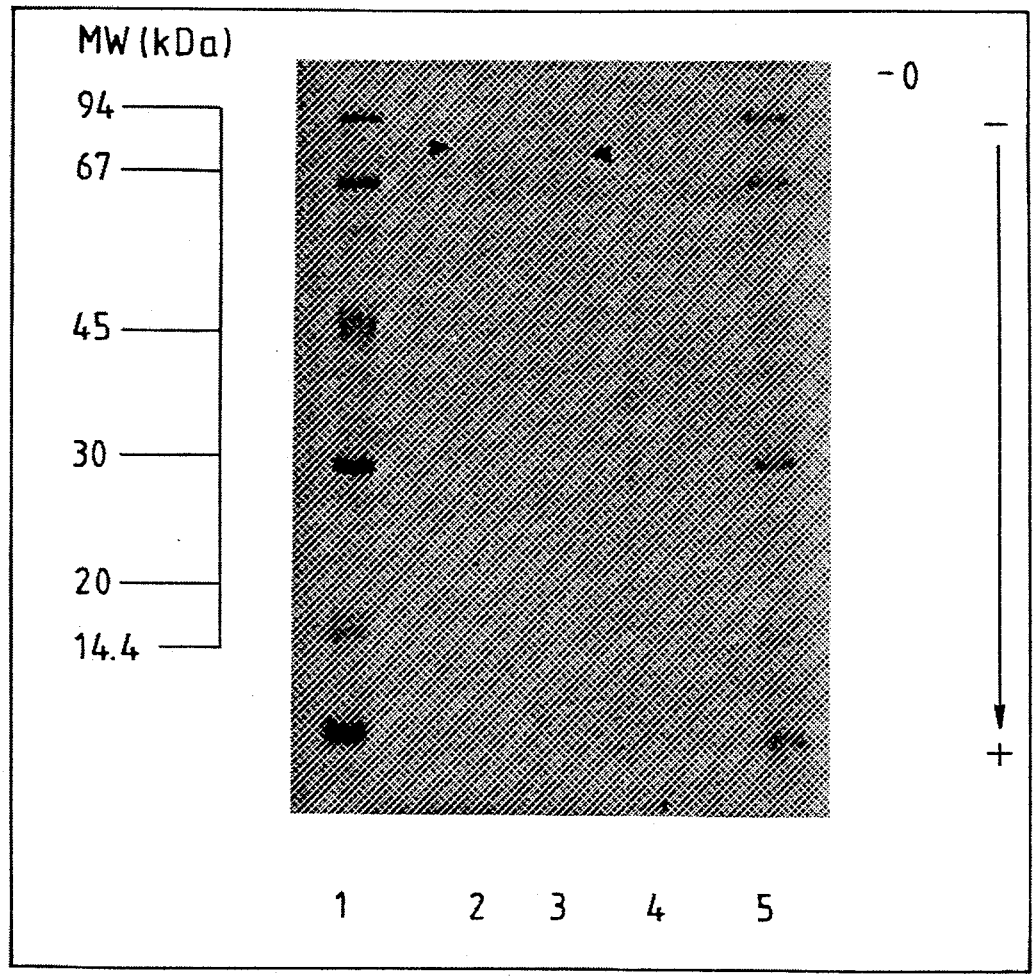

In the case of FIG. 4, electrophoresis was performed on a 12.5% polyacrylamide gel; comparing purified amniotic fluid and maternal serum DAC eluted with heparin from the Cadaverine-Sepharose affinity column. Fewer contaminant proteins were observed in the purified DAO fractions eluted with heparin when compared to those eluted with 1M NaCl as shown in FIG. 3. Estimation of the subunit molecular weight from the calibration curve revealed an amniotic fluid DAO band at 79,000 and a maternal serum DAO band at 75,000. Continuous PAGE was performed on a 7.5% polyacrylamide gel to assess the subunit molecular weight of amniotic fluid and maternal serum DAO eluted with heparin from the Cadaverine-Sepharose affinity column and put through the HPLC gel permeation column. The results for amniotic fluid and maternal serum electrophoresed by continuous PAGE shown in FIG. 5 revealed that a clear difference exists in the subunit structure of the two purified proteins. When the subunit molecular weights were estimated from the calibration curve constructed using the LMW prestained standards, the subunit molecular weight for amniotic fluid DAO was determined to be 79,000, and for maternal serum DAO, 75,000. Determination of the native molecular weight of amniotic fluid and maternal serum DAO by gradient PAGE and HPLC gel permeation revealed that DAO exists as a complex, multisubunit protein. The native molecular weight as was assessed by gradient PAGE for both amniotic fluid DAO and pregnant serum DAO (FIG. 6) revealed molecular weights of 120,000; 160,000 and 480,000. Estimations of the native molecular weights for both proteins by HPLC gel permeation studies also revealed a number of different peaks which displayed enzyme activity and molecular weights approximately the same as those described above as estimated from a calibration curve constructed using gel filtration standards for both amniotic fluid DAO and maternal serum DAO. Similar results were obtained for both amniotic fluid and maternal serum DAO purified by Cadaverine-Sepharose affinity chromatography and eluted from the column with heparin or 1M NaCl (FIG. 6). Variations in the results obtained for the determination of native molecular weight was observed for protein solutions stored for periods of more than 2 weeks at −70° C.

ISOELECTRIC FOCUSING

Figure 7:
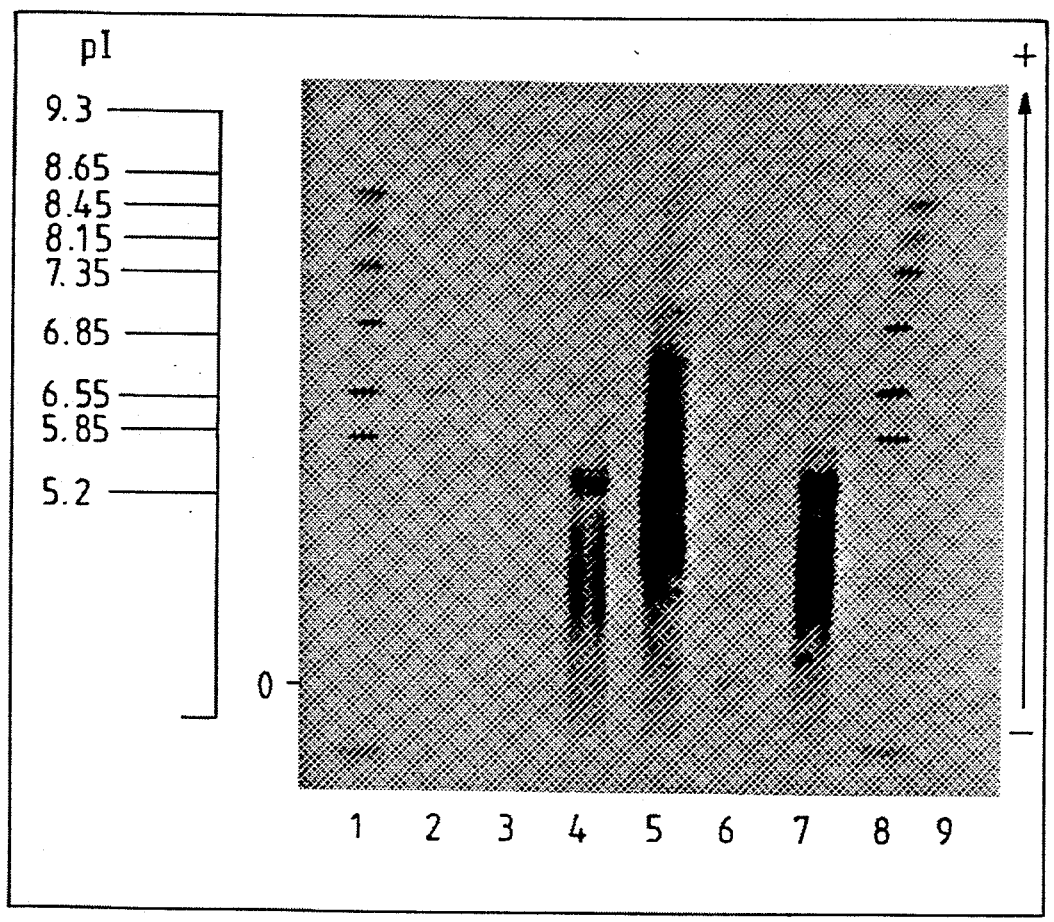

As shown in FIG. 7, maternal serum DAO eluted with heparin (track 4) and IM NaCl (track 7) from the Cadaverine-Sepharose affinity column and put through the HPLC gel permeation column were analysed on an agarose IEF gel with Pharmalyte as the ampholine source. Maternal serum DAO was separated into at least 4 major and many diffuse bands; the isoelectric pH of the major bands for maternal serum DAO ranged from 5.3–5.6, with a large diffuse and acidic tail. A faint diffuse region at 5.75–5.8 was also observed. Amniotic fluid DAO was eluted with heparin (track 6) and 1M NaCl (track 3; faint bands) from the Cadaverine-Sepharose column and put through the HPLC gel permeation column. Amniotic fluid DAO resolved into at least 4 faint bands; the isoelectric pH of these bands ranged from 4.6–5.0. The results of FIG. 8 also showed differences in the separation of amniotic fluid DAO (track 3) and maternal serum DAO (track 4), both of which were eluted from the Cadaverine-Sepharose affinity column with 1M NaCl and put through the PHLC gel permeation column and electrofocused with servalyte as the ampholine source. The protein pattern in track 5 (FIG. 8) is that of maternal serum DAO and track 6 is amniotic fluid DAO (faint), eluted from the DAH-Sepharose affinity column with 0.2M phosphate buffer; amniotic fluid was then further purified by gel filtration through Sephadex G-200.

AGAROSE GEL ELECTROPHORESIS

Figure 9:
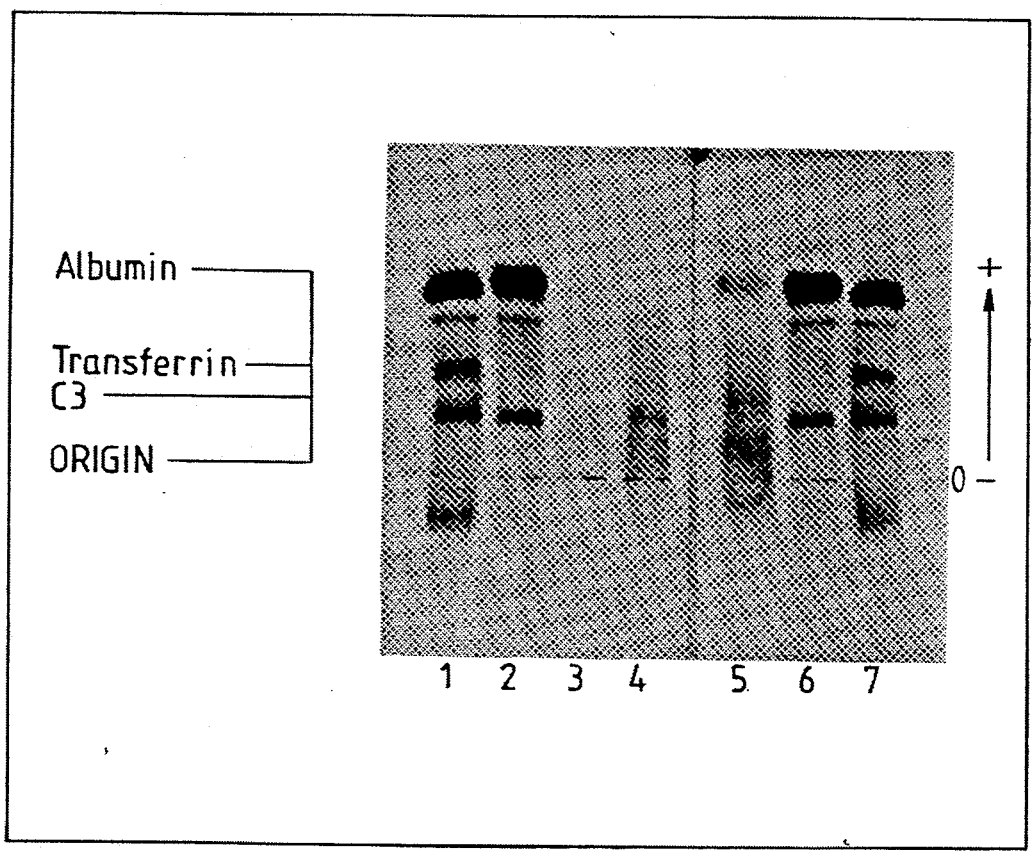
Figure 10:
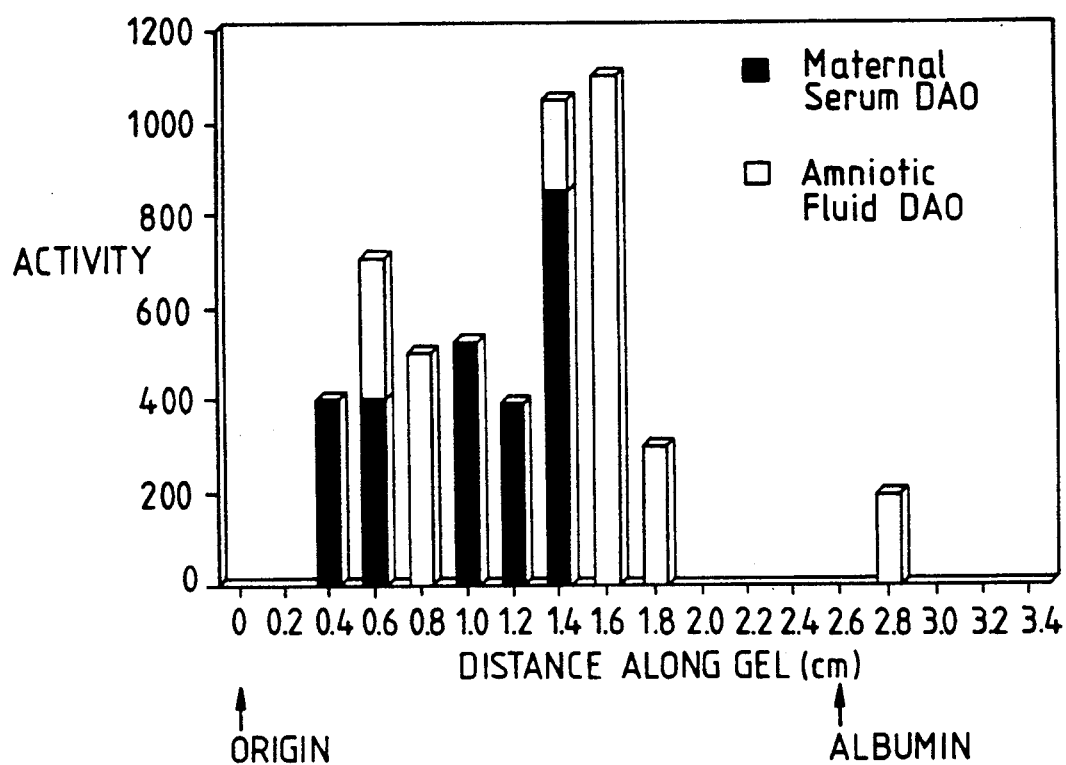

Amniotic fluid and maternal serum DAO eluted with 1000 U of heparin from the Cadaverine-Sepharose affinity column were electrophoresed on a 1% agarose gel as shown in FIG. 9. Maternal serum DAO separated into 3 distinct bands; one band migrated in close proximity to transferrin, the second band migrated in the vicinity of C3, and the third band was located near the origin. Immunofixation performed on purified maternal serum DAO with anti-human C3 (BECKMAN) and anti-human transferrin (KALLESTAD) revealed no visible cross-reactivity with either antisera. Electrophoresis of purified amniotic fluid DAO (heparin eluted) also separated into 3 bands (FIG. 9); the first band migrated in the region between albumin and prealbumin, the second band was observed to a broad band which migrated in the alpha 2-beta globulin region, the third band was observed in the vicinity of the C3 band. Enzyme activity studies were performed on purified amniotic fluid and maternal serum DAO (eluted with 1M NaCl and heparin) electrophoresed on agarose gels (FIG. 10). Results for amniotic fluid DAO as shown in FIG. 10 revealed two areas of enzyme activity which correspond to the 2 bands observed with protein staining (FIG. 9). Lower levels of enzyme activity were also observed with the small amniotic fluid DAO band which had migrated in the region between albumin and prealbumin. This band in particular was more evident in samples of amniotic fluid DAO eluted with heparin, or in samples stored for long periods at −70° C. Enzyme activity studies performed on maternal serum DAO also revealed a number of areas of enzyme activity corresponding to the protein pattern shown in FIG. 9. The majority of the activity for maternal serum DAO was distributed in a broad area; the highest levels of enzyme activity were associated with the band closest to the origin and the band which had migrated in the region of C3. The maternal serum DAO band observed in the region of transferrin displayed variable levels of enzyme activity, which may be accounted for due to the diffuse nature of the band.

IMMUNOFIXATION

Figure 11:
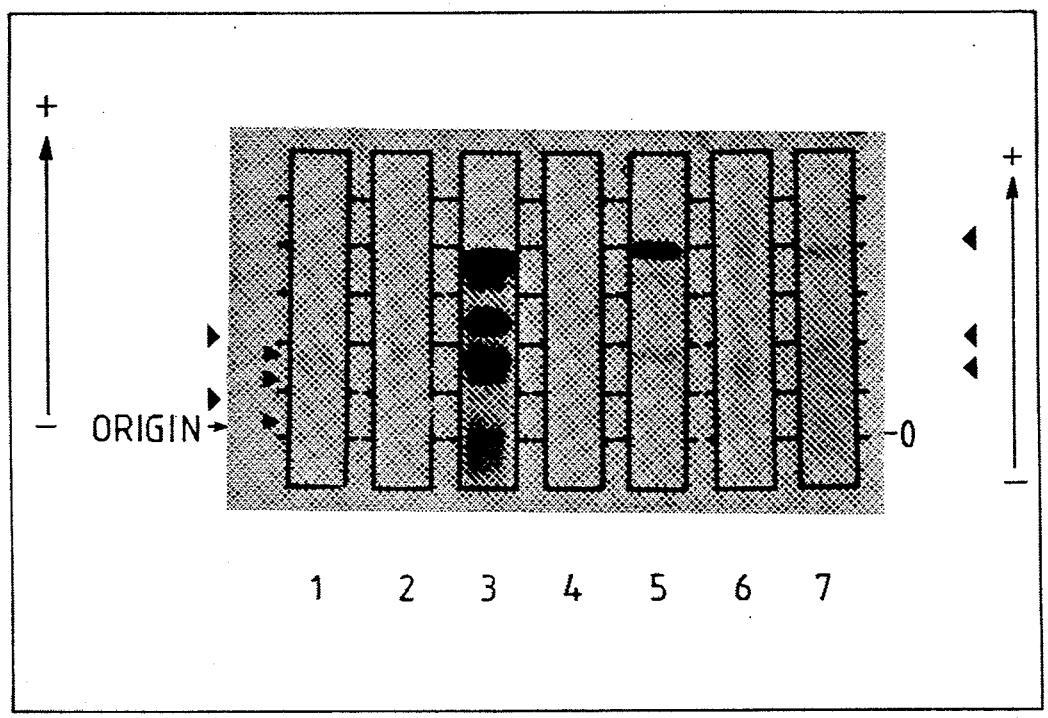

Immunofixation studies were performed using guineapig antihuman amniotic fluid DAO antisera; raised against DAH-Sepharose and Sephadex G-200 purified amniotic fluid DAO. Immunofixation of amniotic fluid and maternal serum DAO with guineapig anti-human amniotic fluid DAO displayed cross-reactivity to both purified enzymes as is shown in FIG. 11. Incubation of the antisera in the presence of maternal serum and maternal serum DAO in the ratio of 50:1:0.3, produced a precipitate which was removed upon centrifugation. The immunoadsorbed antiserum was tested against heparin eluted amniotic fluid and maternal serum DAO.

Figure 12:
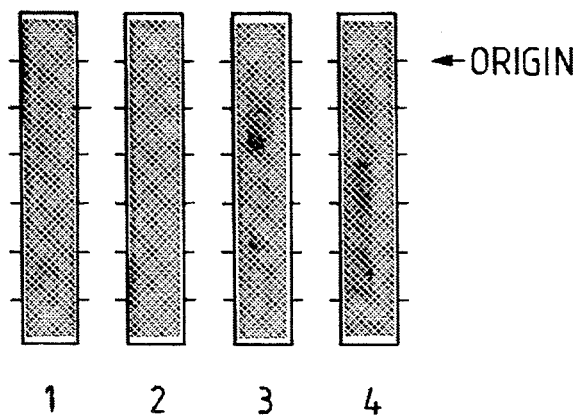

Results of immunofixation performed on Bechman agorose plates with antihuman amniotic fluid DAO antisera which was immunoadsorbed with maternal serum and serum DAO in the ratio of 50:3:1 are shown in FIG. 12. Immunofixation studies with amniotic fluid DAO and serum DAO showed a reaction only with amniotic fluid DAO, with all the activity to serum DAO removed (FIG. 4). The reactivity towards amniotic fluid DAO was directed at the broad band in the region of C3 and to the band located between albumin and prealbumin. Some degree of reactivity was also directed against the amniotic fluid protein band in the alpha 2-beta globulin region.

IMMUNOPRECIPITATION

To examine the specificity of the polyclonal antisera to DAO, maternal serum and amniotic fluid were incubated in the presence of various volumes of polyclonal antisera. From the results shown in FIG. 13, pre-adsorbing maternal serum and amniotic fluid with the polyclonal antisera resulted in the removal of enzyme activity due to the probable formation of antibody-antigen complexes which were removed upon centrifugation.

ASSAY OF VAGINAL FLUID SPECIMENS

Vaginal fluid specimens were collected from two healthy pregnant women who had no clinical evidence of rupture of the amniotic membranes and from one pregnant woman in whom rupture of the membranes was thought to have occurred. A vaginal speculum was passed and fluid collected from the posterior vagina with a sterile syringe. Samples of these fluids (6 μl) were applied to separate wells on an agarose plate (Titan). After electrophoresis, immunoabsorbed polyclonal anti amniotic fluid diamine oxidase specific antiserum was applied to cellulose acetate strips which were overlaid on the agarose in the area of electrophoresed protein. After incubation for 30 minutes in a humidity chamber at room temperature, the strips were removed and the gels were serially dehydrated and washed three times with saline (0.9 G1100 mls) and the remaining immunoprecipitates were visualized with Coomassie Blue.

Figure 14:
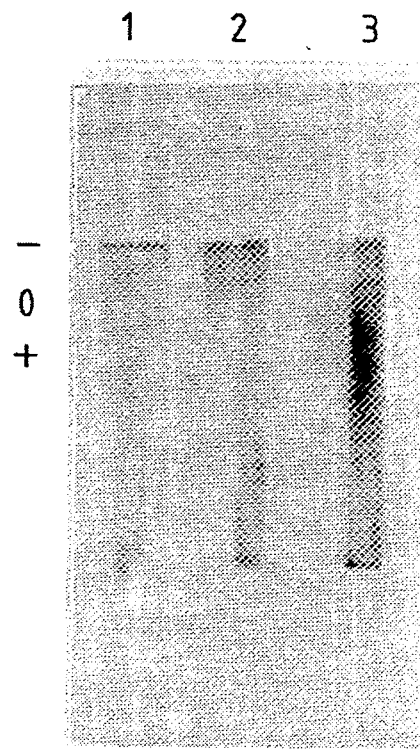

No immunoprecipitate as shown in FIG. 14 was seen in the specimens from the normal women (lanes 1 and 2). Strong immunoprecipitation was observed in the β-legion of the electrophorelogram prepared from the pregnant woman who had clinical evidence of rupture (lane 3) confirming this diagnosis.

THE REFERENCES AS CITED IN THE SPECIFICATION ARE AS FOLLOWS:

Ahlmark, A. (1944). Studies on the Histaminolytic Power of Plasma with Special Reference to Pregnancy. Acta. Physiol. Scand. 9 [Suppl. 18].

Bardsley, W. G., Ashford, J. S. and Hill, C. M. (1971). Synthesis and Oxidation of Aminoalkylonium Compounds by Pig Kidney Diamine Oxidase. Biochem. J. 122: 557–567.

Bardsley, W. G., Crabbe, M. J. C. and Scott, I. V. (1974). The Amine Oxidases of Human Placenta and Pregnancy Plasma. Biochem. J. 139: 169–181.

Baylin, S. B., Abeloff, M. D., Wieman, R. C., Tomford, J. W. and Ettinger, D. S. (1975a). Elevated Histaminase (Diamine Oxidase) Activity in Small-Cell Carcinoma of the Lung. N. Engl. J. Med 293: 1286–1290.

Baylin, S. B. and Margolis, S. (1975b). Purification of Histaminase (Diamine Oxidase) From Human Pregnancy Plasma by Affinity Chromatography. Biochem. Biophys. Acta. 397: 294–306.

Best, C. H. (1929). The Disappearance of Histamine From Autolysing Lung Tissue. J. Physiol. (LONDON). 67: 256–263.

Blaschko, H. (1963) Amine Oxidase. In. The Enzymes, ed. by J. B. Summer and K. Myrbock, Academic Press, Inc., New York. 3: 337–351.

Buffoni, F. (1966). Histamine and Related Amine Oxidases. Pharmacol. Rev. 18: 1163–1199.

Crabbe, M. J. C., Waight, R. D., Bardsley, W. G., Barker, R. W., Kelly, I. D. and Knowles, P. F. (1976). Human Placental Diamine Oxidase: Improved Purification and Characterization of a Copper- and Manganese-Containing Amine Oxidase with Novel Substrate Specificity. Biochem. J. 155: 679–687.

Elmfors, B., Tryding, N. and Tufvesson, G. (1974). The Diagnosis of Ruptured Fetal Membranes by Measurement of the Diamine Oxidase Activity in Vaginal Fluid. J. Obst. Gynecol. Brit. Commonwealth 81: 361–362.

Elmfors, B. and Tryding, N. (1976). Date of confinement Prediction from Serum Diamine Oxidase Determination in Early Pregnancy. Br. J. Obstet. Gynecol. 123: 605–609.

Floris, G., Fadda, M. B., Pellegrini, M., Corda, M. and Finazzi-Agro, A. (1976). Purification of Pig Kidney Diamine Oxidase by Gel-Exclusion Chromatography. FEBS Letters 21: 56–63.

Friedman & McElin. Diagnosis of ruptured fetal membranes, Am. J. Obstet. gynaecol. 48, 172, 1976.

Gahl, W. A., Kozina, T. J., Fuhrmann, D. D. and Vale, A. H. (1982a). Diamine Oxidase in the Diagnosis of Ruptured Fetal Membranes. Obstet. Gynecol. 60(3): 297–304.

Gahl, W. A. Raubertas, R. F., vale, A. M. and Galubjatnikov, R. (1982b). Maternal Serum Diamine Oxidase in Fetal Death and Low Birthweight Infants. Br. J. Obstet. Gynaecol. 89: 202–207.

Hata, A. (1976). Purification and Some Properties of Diamine Oxidase from Pig Kidney and Human Placenta. Bull. Tokyo Med. Dent. Univ. 23: 63–70.

Kapeller-Adler, R. and MacFarlane, H. (1963). Purification and Identification of Hog-Kidney Histaminase. Biochim. Biophys. Acta 67: 542–565.

Klimova, G. I., Gromova, L. N. and Gorkin, V. Z. (1976). Sorbent for the Purification of Diamine Oxidase by Affinity Chromatography. Appl. Biochem. Micr. (MOSCOW). 12: 614–618.

Kluetz, M. D. and Schmidt, P. G. (1977). Diamine Oxidase: Molecular Weight and Subunit Analysis. Biochem. Biophys. Res. Comm. 76: 40–45.

Laemmli, U. K. (197). Cleavage of Structural Proteins During the Assembly of the Head of Bacteriophage T4. Nature 227: 680–685.

Lin, C. -W., Kirley, S. D. and St. Pierre, M. (1981). Tumor and Placental Histaminase: Affinity Chromatography, Purification and Characterization of the Placental Enzyme. Oncodev. Biol. Med. 2: 267–280.

Larsen, Premature rupture of the membranes, Br. Med. J., 1, 1165, 1979.

Lorenz, Kusche, et a, Diaminoxidase, methoden den enzymatischen anayse, 2nd Ed.

Mondovi, B., Rotilio, G., Finazzi-Agro, A. and Scioscia-Santora, A. (1964). Purification of Pig Kidney Diamine Oxidase and Its Identity with Histaminase. Biochem. J. 91: 408–415.

Mondovi, B., Rotilio, G., Costa, M. T., Finazzi-Agro, A., Chiancone, F., Hansen, R. E. and Beinert, H. (1967). Diamine Oxidase From Pig Kidney. Improved Purification and Properties. J. Biol. Chem. 242: 1160–1167.

Overstreet and Romney, Am. J. Obstet. Gynaecol., 96, 1036, 1966.

Paolucci, F., Cronenberger, L., Plan, R. and Pacheco, H. (1971). Purification et Proprietes de la Diamine: Oxygene Oxydo-Reductase du Placenta Humain. Biochimie 53: 735–749.

Shindler, J. S. and Bardsley, W. G. (1976). Human Kidney Diamine Oxidase: Inhibition Studies. Biochem. Pharm. 25: 2689–2694.

Smith, J. K. (1967). The Purification and Properties of Placental Histaminase. Biochem. J. 103: 110–119.

Swanberg, H. (1950). Histaminase in Pregnancy with Special Reference to Its Origin and Formation. Acta Physiol. Scand. 23 (Suppl 79): 1–69.

Swartz, Napolitani, et al, Controversy in obstetrics and gynecology, Ed. D. E. Reid and T. C. Bacon, Saunders, Philadelphia, London, Toronto, 46, 1969.

Tornqvist, A., Jonassen, F., Johnson, P. and Fredholm, A. (1971). Studies on Diamine Oxidase Activity During Pregnancy. Acta Obstet. Gynec. Scand. 50: 79–82.

Tufvesson, G. (1978a). Purification and Properties of Human Amniotic Fluid Diamine Oxidase. Scand. J. Clin. Lab. Invest. 38: 463–472.

Tufvesson, G. (1978b). A Comparison Between Diamine Oxidases From Human Post-Heparin Blood Serum, Pregnancy Blood Serum and Amniotic Fluid. Scand. J. Clin. Lab. Invest. 38: 473–476.

Uspenskaia, V. D. and Goriachenkova, E. V. (1958). The Purification of Diamine Oxidase by Electrophoresis. Biokhimiya 23: 199–205.

Wishart, H. M., Jenkins, D. T. and Knott, M. C. (1979). Measurement of Diamine Oxidase Activity in Vaginal Fluid-An Aid to Diagnosis of Ruptured Fetal Membranes. Aust. N. Z. J. Obstet. Gynaec. 19: 23–24.

Yamada, H., Kumagai, H., Kawasaki, H., Matsui, H. and Ogata, K. (1967). Crystallization and Properties of Diamine Oxidase From Pig Kidney. Biochem Biophys. Res. Comm 29: 723–727.

Zeller, E. A. (1965). Identity of Histaminase and Diamine Oxidase. Fed. Proc. 24: 766–768.

DESCRIPTION OF FIGS. 1–14

FIG. 1. Phosphate salt inhibition of amniotic fluid DAO (O) and maternal serum DAO (X). The increasing phosphate salt concentrations were substituted for the 1/15M phosphate buffer, pH 7.4, used in the radioenzymatic assay.

Figure 2:
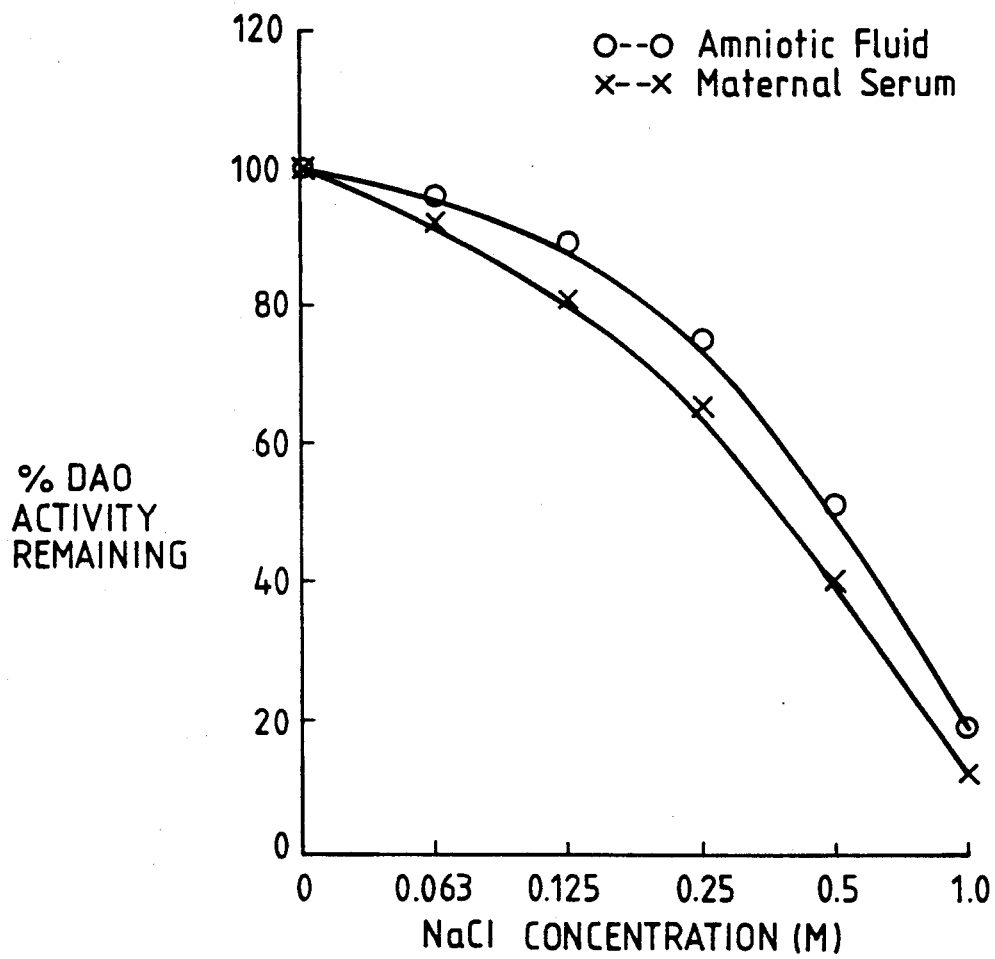

FIG. 2. Salt inhibition of amniotic fluid DAP (O) and maternal serum DAO (X). The increasing salt concentrations were prepared in the 1/15M phosphate buffer, pH 7.4, used in the radioenzymatic assay.

FIG. 3. Sodium dodecyl sulfate gel electrophoresis on a 10% polyacrylamide gel of purified maternal serum DAO (lane 5, ←) and amniotic fluid DAO (lane 4, →) eluted with 1M NaCl from the Cadaverine-Sepharoe affinity column. These were compared to maternal serum DAO (lane 6) and amniotic fluid DAO (lane 1) purified by DAH-Sepharose affinity chromatography. Calibration curves were constructed from the protein markers in lane 2 (LMW standards, PHARMACIA) and lanes 3 and 7 (SDS-PAGE LMW standards, BIORAD).

FIG. 4. Sodium dodecyl sulfate gel electrophoresis on a 12.5% polyacrylamide gel of purified maternal serum DAO (lane 3, ←) eluted with heparin from the Cadaverine-Sepharose affinity column. Amniotic fluid DAO was purified by heparin (lane 2, →) and 1M NaCl (lane 4) elution from the Cadaverine-Sepharose affinity column. Calibration curves were constructed from the protein markers in lanes 1 and 5 (LMW standards, PHARMACIA).

Figure 5:
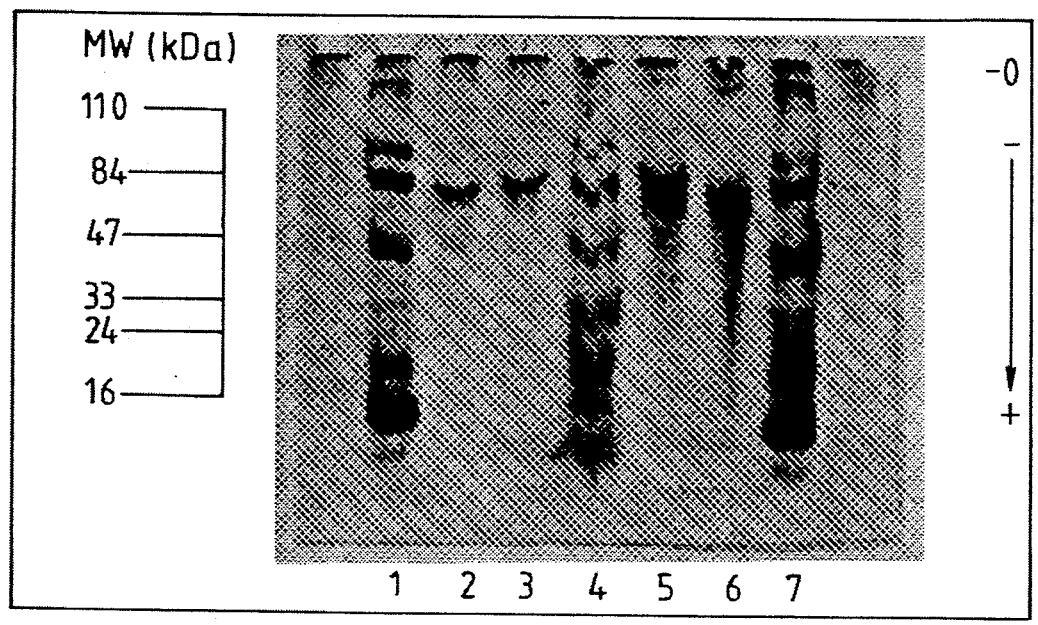
Figure 6:
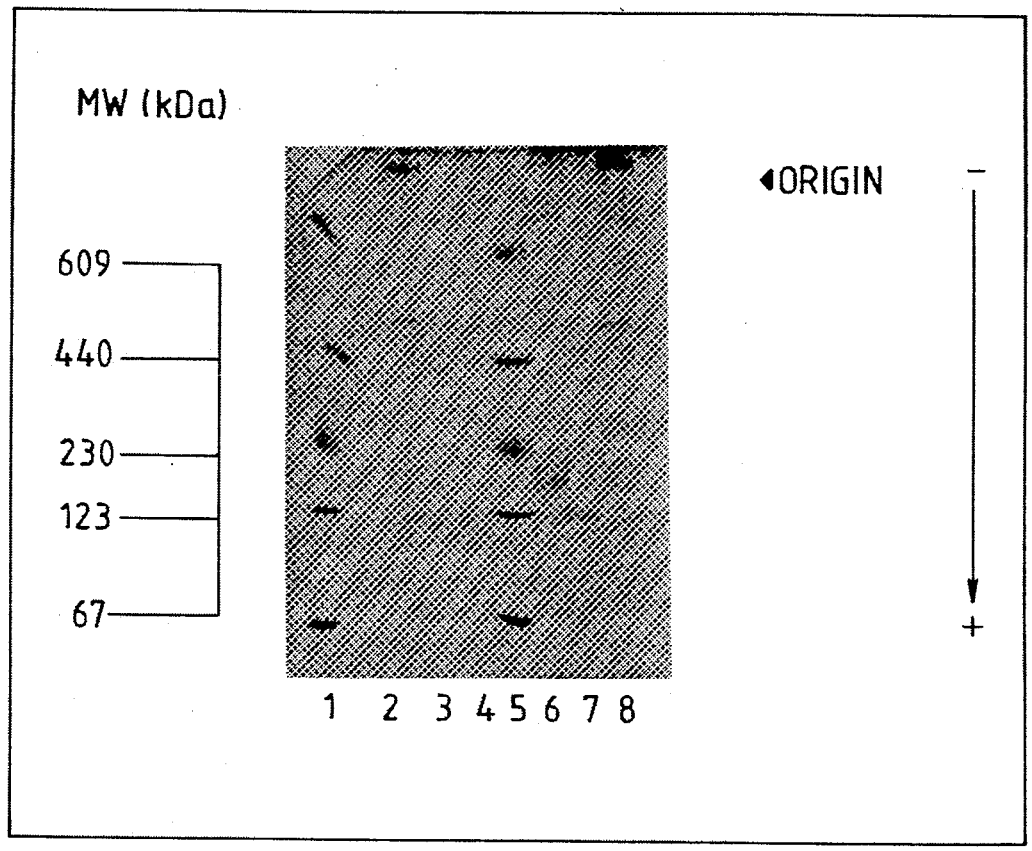

FIG. 5. Continuous sodium dodecyl sulfate gel electrophoresis on a 7.5% continuous polyacrylamide gel of purified maternalserum DAO eluted with heparin (lane 2) and 1M NaCl (lane 5), with purified amniotic fluid DAO eluted with heparin (lane 3) and 1M NaCl (lane 6) The proteins were eluted from the Cadaverine-Sepharose affinity column and further purified by HPLC gel permeation chromatography. Calibration curves were constructed from the protein markers in lanes 1 and 7 (LMW standards, PHARMACIA) and lane 4 (Prestained SDS-PAGE standards, BIORAD).

FIG. 6. Gradient gel electrophoresis performed on a PAA 4/30 polyacrylamide gel on purified maternal serum DAO eluted with heparin (lane 3) and 1M NaCl (lane 6), and purified amniotic fluid DAO eluted with heparin (lanes 4 and 7) and 1M NaCl (lanes 2 and 8). The proteins were eluted from the Cadaverine-Sepharose affinity column; calibration curves were constructed from the protein markers in lanes 1 and 5 (HMW standards, PHARMACIA).

FIG. 7. Agarose IEF performed in pH 3-10 Pharmalyte. Samples of maternal serum DAO purified by heparin (lane 4) and 1M NaCl (lane 7), and amniotic fluid DAO purified by heparin (lane 6) and 1M NaCl [(lane 3) faint bands], were eluted from the Cadaverine-Sepharose affinity column and put through the HPLC gel permeation column. The protein pattern in lane 5 is that of material serum DAO purified by DAH-Sepharose affinity chromatography. The calibration curves were constructed from the broad pH range [(pH range 3-10), lanes 1 and 8] and low pH range [(pH range 2.5-6.5), lanes 2 and 9] standard proteins (PHARMACIA).

Figure 8:
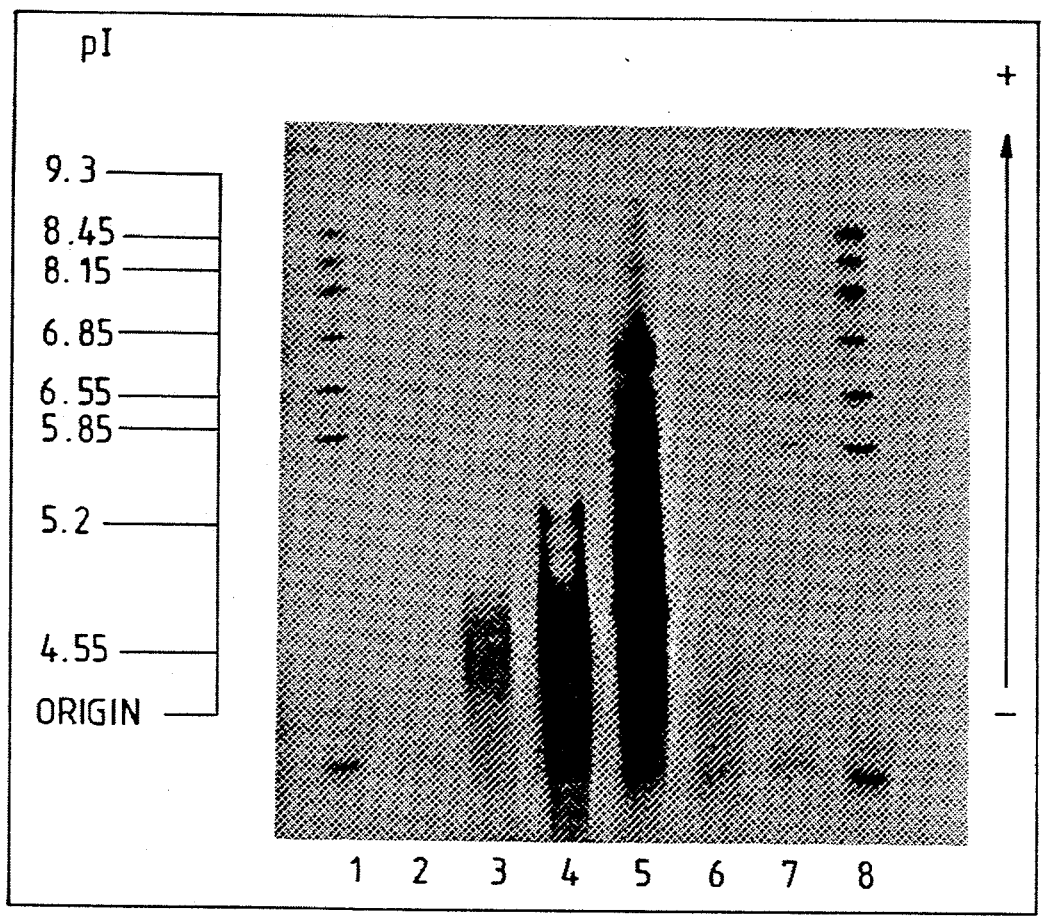

FIG. 8. Agarose IEF performed in pH 4-9 Servalyte. Samples of material serum DAO eluted with 1M NaCl (lane 4) and amniotic fluid DAO eluted with 1M NaCl (lane 3) from the Cadaverine-Sephraose affinity column and put through the HPLC gel permeation column. These patterns were compared with maternal serum DAO (lane 5) and amniotic fluid DAO (lane 6) purified by DAH-Sepharose and Sephadex G-200 chromatography. The calibration curves were constructed from the broad pH range [(pH range 3-10) lanes 1 and 8] and low pH range [(pH range 2.5-6.5) lanes 2 and 7] standard proteins (PHARMACIA).

FIG. 9. Agarose gel electrophoresis performed on Cadaverine-Sepharose purified maternal serum DAO (heparin eluted, lane 4) and amniotic fluid DAO eluted with heparin (lane 5) and 1M NaCl (lane 3). The purified protein patterns were compared to those of maternal serum (lanes 1 and 7) and amniotic fluid (lanes 2 and 5).

FIG. 10. Activity studies performed on amniotic fluid DAO and maternal serum DAO. Both species of DAO were purified by heparin elution off the Cadaverine-Sepharose affinity column and electrophoresed on a 1% agarose gel. Enzyme activity (dpm) was determined from sectioned gels by radioenzymatic analysis.

FIG. 11. Immunofixation and protein electrophoresis on agarose gels. Immunofixation patterns of amniotic fluid (lane 6) and maternal serum (lane 2) after incubation with polyclonal antisera. Polyclonal antisera immunoabsorbed with maternal serum and purified maternal serum DAO in a ratio of 50:1:0.3 removed all activity towards maternal serum (lane 4). In direct comparison, purified samples of DAO eluted with heparin off the Cadaverine-Sepharose column from amniotic fluid (lane 7, ◄) and maternal serum (lane 1, ►) were run on the same gel and stained for proteins. Maternal serum (lane 3) and amniotic fluid (lane 5) were also protein stained as markers.

FIG. 12. Approximately 30 ug of protein was applied to the Beckman gel and electrophoresed prior to application of the antihuman amniotic fluid DAO antisera. Antihuman amniotic fluid DAO antisera was then applied to cellulose acetate strips which were then placed onto the gel over the area of protein electrophoresis. The samples were; maternal serum (1), serum DAO (2), amniotic fluid DAO (3) and native amniotic fluid (4).

Figure 13:
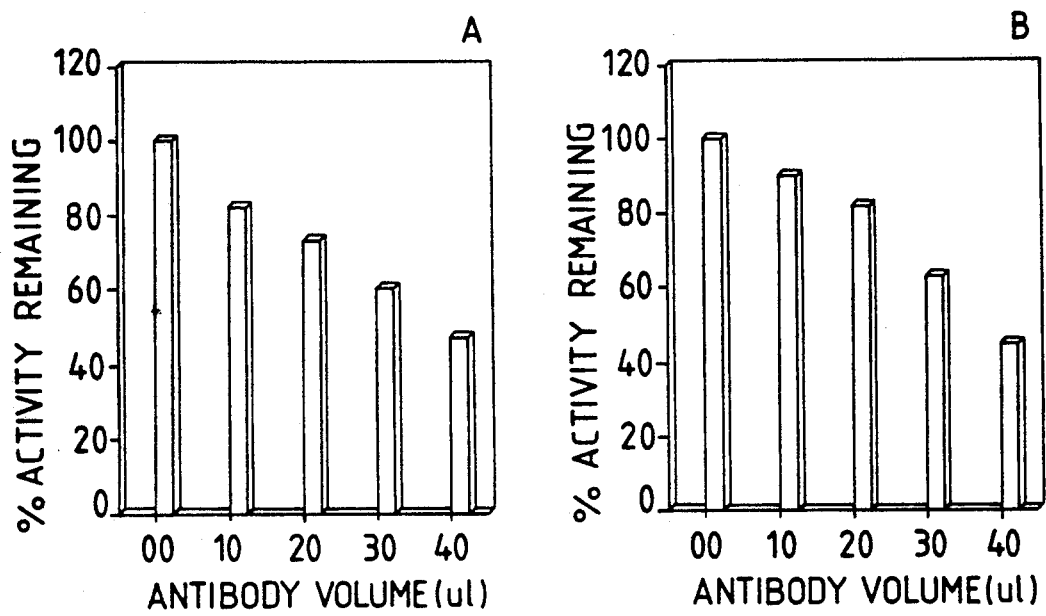

FIG. 13. Immunoprecipitation of amniotic fluid and maternal serum by incubation of 0.5 ml of both fluids with the different volumes of the monoclonal antibody and polyclonal antisera. The immunoprecipitate was removed by centrifugation and the remaining enzyme activity was determined by radioenzymatic analysis.

FIG. 14. Immunofixation performed on three patient samples using the immunoabsorbed antiserum specific for amniotic fluid diamine oxidase. Samples from two normal patients are shown in lanes 1 and 2 and a sample from a patient suspected clinically of having ruptured the amniotic membrane is shown in lane 3.

We claim:

1. An assay suitable for the diagnosis of rupture of an amniotic membrane in a pregnant mammal or leakage of amniotic fluid by reacting with an antibody derived from amniotic fluid diamine oxidase, said assay comprising the steps of:
   detecting the presence of amniotic fluid diamine oxidase in vaginal fluid; and
   distinguishing said amniotic fluid diamine oxidase from serum diamine oxidase.

2. An assay as claimed in claim 1, and further including the step of developing a polyclonal or monoclonal antibody to serum diamine oxidase or amniotic fluid diamine oxidase or both.

3. An assay as claimed in claim 2, wherein polyclonal antiserum is developed to amniotic fluid diamine oxidase which is subsequently immunoabsorbed with maternal serum and purified serum diamine oxidase before immunofixation with vaginal fluid.

4. An assay suitable for the detection of amniotic fluid diamine oxidase in a body fluid, said assay comprising the step of testing for the presence of amniotic fluid diamine oxidase in said body fluid by reacting with an antibody derived from amniotic fluid diamine oxidase and distinguishing said amniotic fluid diamine oxidase from serum diamine oxidase.

5. An assay suitable for the detection of diagnosis of rupture of an amniotic membrane in a pregnant mammal, said assay comprising the steps of:
   obtaining a sample of vaginal fluid from a pregnant female;
   reacting said sample with antibody derived from amniotic fluid diamine oxidase; and
   detecting reactivity with a signal amplification.

6. An assay suitable for diagnosis of rupture of an amniotic membrane in a pregnant woman or leakage of amniotic fluid, said assay comprising the steps of:
   obtaining a sample of vaginal fluid from a pregnant woman;
   reacting the sample with antibody derived from a purified form of amniotic fluid diamine oxidase which has the following physical properties:
   (i) a subunit molecular weight of approximately 79,000 determined by SDA-PAGE with gels of different acrylamide concentrations;
   (ii) a number of species of molecular weight 120,000; 160,000 and 480,000 daltons as revealed by a native molecular weight determination via gradient-PAGE or gel filtration chromatography;
   (iii) a pattern characteristic of glycoproteins with the isoelectric points of the bands being generally below 5.0 as determined by isoelectric focusing;
   (iv) multiple bands of activity different to the bands corresponding to maternal serum diamine oxidase when the purified enzyme is analyzed by electrophoresis on agarose gels and immunofixation with polyclonal antisera raised to amniotic fluid diamine oxidase; and
   (v) removal of all reactivity to the maternal serum proteins when tested by immunofixation but reactivity being retained to amniotic fluid diamine oxidase upon immunoadsorption of the polyclonal antiserum raised to amniotic fluid diamine oxidase with maternal serum and purified maternal serum diamine oxidase; and
   detecting the presence of amniotic fluid in the vaginal sample by detecting the reaction of amniotic fluid diamine oxidase in the amniotic fluid with an antibody raised to the amniotic fluid form of diamine oxidase which antibody does not react with maternal serum diamine oxidase.

7. An assay as claimed in claim 6, wherein the antibody is polyclonal antiserum which is immunoadsorbed with maternal serum before reaction with the vaginal fluid.

8. An assay as claimed in claim 6, wherein the polyclonal antiserum is immunoadsorbed with maternal serum and maternal serum diamine oxidase having the following physical properties:
   (i) a molecular weight of approximately 75,000 performed by SDS-PAGE with gels of different acrylamine concentrations;
   (ii) a number of species with molecular weights or 120,000; 160,000 and 480,000 daltons as revealed by a native molecular weight analysis via gradient-PAGE or gel filtration chromatography;
   (iii) a pattern characteristic of a glycoprotein and with substantial bands with isoelectric points greater than 5 revealed by isoelectric focussing;
   (iv) multiple bands of activity different to those bands corresponding to amniotic fluid diamine oxidase when the purified enzyme is analyzed by electrophoresis on agarose gels and immunofixation with polyclonal antisera raised to amniotic fluid diamine oxidase; and
   (v) lack of reactivity with a polyclonal antiserum raised to amniotic fluid diamine oxidase and immunoadsorbed with maternal serum and purified maternal serum diamine oxidase when tested by immunofixation.

9. A diagnostic test kit suitable for diagnosis of rupture of an amniotic membrane in a pregnant mammal or leakage of amniotic fluid, said kit comprising:
   a first antibody selected from amniotic fluid diamine oxidase antibody and serum diamine oxidase antibody immobilized to an inert surface; and
   a second tag antibody having a label attached thereto.

10. A kit as claimed in claim 9, wherein said first antibody is a monoclonal or polyclonal antibody.

11. A kit as claimed in claim 9, wherein said second tag antibody is a monoclonal or polyclonal antibody for serum diamine oxidase and amniotic fluid diamine oxidase.

* * * * *